(12) United States Patent
Sasaki et al.

(10) Patent No.: US 8,470,311 B2
(45) Date of Patent: *Jun. 25, 2013

(54) THERAPEUTIC AGENT FOR ANAEROBIC DISEASES

(75) Inventors: Takayuki Sasaki, Nagano (JP); Hitomi Shimizu, Nagano (JP); Yuko Shimatani-Shibata, Nagano (JP); Hiromi Yonekura, Suwa (JP)

(73) Assignee: Anaeropharma Science, Inc., Tokyo (JP)

( * ) Notice: Subject to any disclaimer, the term of this patent is extended or adjusted under 35 U.S.C. 154(b) by 235 days.

This patent is subject to a terminal disclaimer.

(21) Appl. No.: 12/988,181

(22) PCT Filed: Apr. 17, 2009

(86) PCT No.: PCT/JP2009/001776
§ 371 (c)(1),
(2), (4) Date: Dec. 22, 2010

(87) PCT Pub. No.: WO2009/128275
PCT Pub. Date: Oct. 22, 2009

(65) Prior Publication Data
US 2011/0110893 A1    May 12, 2011

Related U.S. Application Data

(60) Provisional application No. 61/124,528, filed on Apr. 17, 2008.

(51) Int. Cl.
| | |
|---|---|
| A61K 35/74 | (2006.01) |
| C07H 3/04 | (2006.01) |
| C07H 3/06 | (2006.01) |
| C12N 1/38 | (2006.01) |
| A61P 35/00 | (2006.01) |
| A61P 9/10 | (2006.01) |

(52) U.S. Cl.
USPC ............... 424/93.2; 536/123.13; 536/123.1; 536/1.11; 435/244

(58) Field of Classification Search
None
See application file for complete search history.

(56) References Cited

U.S. PATENT DOCUMENTS

| 6,416,754 B1 | 7/2002 | Brown et al. |
| 6,652,849 B2 | 11/2003 | Brown et al. |
| 2003/0103952 A1 | 6/2003 | Brown et al. |
| 2005/0025745 A1 | 2/2005 | Fujimori et al. |
| 2009/0176747 A1* | 7/2009 | Pommier et al. .............. 514/154 |
| 2009/0264513 A1* | 10/2009 | Shimatani-Shibata et al. . 514/44 R |

FOREIGN PATENT DOCUMENTS

| EP | 1 867 714 | 12/2007 |
| JP | 2002-097144 | 4/2002 |
| WO | WO 2006/057289 | 6/2006 |
| WO | WO 2007/136107 | 11/2007 |

OTHER PUBLICATIONS

Honda et al. (PNAS, Jan. 1991; 88: 179-183).*
Corneau et al (Plasmid. 2004; 51: 87-100).*
Shoemaker et al (Applied and Environmental Microbiology 1991, pp. 2114-2120).*
Gokara et al. (American Chemical Society. Fuels and Chemicals from Biomass. ACS Symposium Series. 1997; Ch.13).*
Mead, et al., "Single-stranded DNA "blue" T7 promoter plasmids: a versatile tandem promoter system for cloning and protein engineering", Protein Eng., vol. 1, No. 1, pp. 67-74, 1986.
Argnani, et al., "A convenient and reproducible method to genetically transform bacteria of the genus *Bifidobacterium*", Microbiology, 142, pp. 109-114, 1996.
Matsumura, et al., "Construction of *Escherichia coli-Bifidobacterium longum* shuttle vector transforming *B. longum* 105-A and 108-A", Biosci. Biotech Biochem, 61(7), pp. 1211-1212, 1997.
Tanaka, et al., "Structural and functional analysis of pTB6 from *Bifidobacterium longum*", Biosci. Biotech. Biochem., 69(2), pp. 422-425, 2005.
Yazawa, et al., "*Bifidobacterium longum* as a delivery system for cancer gene therapy: Selective localization and growth in hypoxic tumors", Cancer Gene Therapy, 7(2), pp. 269-274, 2000.
Yaza Wa, et al., "*Bifidobacterium longum* as a delivery system for gene therapy of chemically induced rat mammary tumors", Breast Cancer Res. Treatment, 66, pp. 165-170, 2001.

* cited by examiner

*Primary Examiner* — Scott Long
(74) *Attorney, Agent, or Firm* — Jones Day

(57) ABSTRACT

The present invention provides a therapeutic agent for anaerobic diseases such as solid tumor, comprising in combination a pharmaceutical composition for the treatment of an anaerobic disease containing the transformed anaerobic microorganism as an active component and a pharmaceutical composition containing as an active component an anaerobic microorganism colonization and growth enhancer for enhancing the specific colonization and proliferation of the anaerobic microorganism at an anaerobic disease site. Furthermore, the present invention provides to an anaerobic microorganism colonization and growth enhancer for enhancing colonization and growth of the transformed anaerobic microorganism at a disease site that is in an anaerobic environment.

20 Claims, 2 Drawing Sheets

THERAPEUTIC AGENT FOR ANAEROBIC DISEASES

CROSS-REFERENCE TO RELATED APPLICATIONS

This application is a national stage filing under 35 U.S.C. §371 of International Application No. PCT/JP2009/001776, filed on Apr. 17, 2009, which claims the benefit of priority of U.S. provisional application No. 61/124,528, filed on Apr. 17, 2008. The entireties of U.S. provisional application No. 61/124,528 and International Application No. PCT/JP2009/001776 are incorporated in this application by reference.

TECHNICAL FIELD

Field of the Invention

The present invention relates to a therapeutic agent for anaerobic diseases comprising a novel transformed anaerobic microorganism, the therapeutic agent containing in combination a pharmaceutical composition for the treatment of an anaerobic disease containing the transformed anaerobic microorganism as an active component and a pharmaceutical composition containing as an active component an anaerobic microorganism colonization and growth enhancer for enhancing the colonization and proliferation of the anaerobic microorganism at an anaerobic disease site. Furthermore, the present invention relates to an anaerobic microorganism colonization and growth enhancer for enhancing colonization and growth of the transformed anaerobic microorganism at a disease site that is in an anaerobic environment.

BACKGROUND ART

Background of the Invention

In recent years, as a method for treating a disease that is in an anaerobic environment (hereinafter, called an 'anaerobic disease') such as a malignant tumor or an ischemic disease, for example, as a method for treating a solid tumor, a method using a transformed anaerobic microorganism as a gene transporter has been attracting an attention. For example, a method of transporting a gene to a tumor site using transformed *Clostridium* has been proposed (see e.g. U.S. Pat. Nos. 6,416,754 and 6,652,849, and US Patent Application Publication 2003/0103952). Furthermore, the application of transformed *Bifidobacterium* (*B.*) *longum* to the treatment of solid tumors has been proposed (see e.g. JP A 2002-97144, Yazawa et al., Cancer Gene Ther., 7, 269-274 (2000), Yazawa et al., Breast Cancer Res. Treat., 66, 165-170 (2001)).

These transformed microorganisms are generated using expression vectors such as the shuttle plasmids pNTR500F, pCD540FT, etc., which are replicated in both *E. coli* and *Clostridium* (U.S. Pat. Nos. 6,416,754 and 6,652,849, and US Patent Application Publication 2003/0103952) or the shuttle plasmid pBLES100-S-eCD, which is replicated in both *E. coli* and *Bifidobacterium* (JP A 2002-97144). Since all of these plasmid vectors are shuttle vectors that are replicated in both *E. coli* and the transformed *Clostridium* or *Bifidobacterium*, the bacteria that have been transformed with these plasmid vectors has the risk that the introduced gene may horizontally transferred to other microorganisms other than the transformed bacterium, at least *E. coli*, which is facultatively anaerobic, and environmental risks and problems in actual treatment are concerned.

Furthermore, JP A 2002-97144 describes that *B. longum* can selectively be made to proliferate in the tumor tissue by intraperitoneally administering lactulose to the mouse to which *B. longum* has been administered. However, the transformant described therein is transformed using a plasmid vector that can be horizontally transferred to other anaerobic *E. coli*, etc., and there are still problems remaining for its safe and effective use in the treatment of an anaerobic disease.

SUMMARY OF INVENTION

Technical Problem

In a method for treating an anaerobic disease using a transformed anaerobic microorganism, it is necessary that the transformed anaerobic microorganism to be used is non-pathogenic and nontoxic, colonizes and grows only in diseased tissue that is in an anaerobic state, but does not colonize or grow in normal tissue that is not in an anaerobic state, as well as that the gene introduced into the transformed anaerobic microorganism is not to be horizontally transferred to pathogenic bacteria or aerobic or facultatively anaerobic bacteria other than the transformed anaerobic microorganism.

Furthermore, in order that a method for treating an anaerobic disease using a transformed anaerobic microorganism fully exhibits its therapeutic effect, the transformed anaerobic microorganism to be used is required not only to specifically colonize at the anaerobic disease site, but also to proliferate to a therapeutically effective amount, and to be continuously present during the treatment period until its completion. On the other hand, since viable cells are administered intravenously or into diseased tissue, the dose of the transformed anaerobic microorganism is preferably as small as possible in order to minimize the influence within blood vessels and the burden on a patient, and therefore, it is desirable that transformed anaerobic microorganism specifically proliferate at the anaerobic disease site and to the therapeutically effective amount by the minimum necessary dosage.

The object of the present invention is therefore to provide a therapeutic agent for anaerobic diseases that, in a method for treating an anaerobic disease using a transformed anaerobic microorganism, is safe and practical, and can exhibit an effect with a small dose.

Solution to Problem

The present inventors have carried out an intensive investigation in order to solve the above problems, and have improved the shuttle plasmid pBLES100-S-eCD to construct the plasmid pAV001-HU-eCD-M968 (see, WO 2007-136107). The inventors have further improved this plasmid by removing from it pUC ori, which is a fragment containing an origin of replication for *E. coli*, to construct the plasmid pBifiCD (see, U.S. provisional application No. 61/124,528). Since this plasmid does not contain the origin of replication of *E. coli*, a bacterium transformed with this plasmid does not have the risk of being replicated in *E. coli*, even if horizontal transfer to *E. coli* occurs. It is therefore an extremely safe transformed anaerobic microorganism, and can be used as a practical therapeutic agent for an anaerobic disease. A bacterium transformed by this plasmid, for example, *B. longum* 105-A/pBifiCD (National Institute of Technology and Evaluation Patent Microorganisms Depositary (hereinafter called NPMD, 2-5-8 Kazusakamatari Kisarazu-city Chiba 292-0818 Japan, Date of deposit: 19 Feb. 2008,) Accession Number NITE BP-491) exhibits a good cytosine deaminase (CD) expression activity, and by using it in combination with the prodrug 5-FC, which is converted by said CD into the antitumor substance 5-FU, a very marked tumor growth suppression effect is exhibited, and it is promising as an excellent tumor treatment agent. However, the present inventors have found another problem, in that such transformed bacteria do not have sufficient colonization and growth capability in the tissue of the organism, and in order to transport an amount of target gene sufficient for the treatment of an anaerobic disease to target tissue such as a solid tumor it is necessary to administer a relatively large amount of transformed bacteria. Therefore, from the viewpoint of safety and cost, a method for making the bacteria to efficiently colonize and proliferate is also necessary.

As a result of an intensive investigation by the present inventors for the purpose of improving the utility as an anaerobic disease therapeutic agent of a pharmaceutical composition containing, for example, the *B. longum* 105-A/pBifiCD (NPMD Accession Number: NITE BP-491) as an active component, it has been found that the use of such a transformed anaerobic microorganism in combination with a pharmaceutical composition containing a certain type of saccharide as an active component remarkably promote the specific colonization and proliferation of the microorganism at an anaerobic disease site, and, furthermore, the proliferation of the microorganism at the anaerobic disease site can be sustained and the therapeutic effect can be markedly enhanced. The present inventors also have found that by using such saccharide in combination, even a reduced dose of the transformed anaerobic microorganism for the treatment of an anaerobic disease can give the same therapeutic effects as a high dose, thereby improving the safety as an anaerobic disease therapeutic agent. Furthermore, since these saccharides promote at an anaerobic disease site colonization and growth of the transformed anaerobic microorganism for the treatment of an anaerobic disease of the present invention, they can become an excellent anaerobic microorganism colonization and growth enhancer. As a result of a further investigation by the present inventors based on the above findings, the present invention has been accomplished.

That is, the present invention relates to (1) an anaerobic disease therapeutic agent containing in combination a pharmaceutical composition comprising as an active component a transformed anaerobic microorganism being transformed by an expression vector that functions in the anaerobic microorganism, the expression vector not containing a plasmid replication unit that functions in *E. coli*, and a pharmaceutical composition comprising as an active component a colonization and proliferation enhancer for the transformed anaerobic microorganism at an anaerobic disease site, (2) the therapeutic agent according to (1), wherein the expression vector comprises 1) a plasmid replication unit that functions in an anaerobic microorganism other than *E. coli*, and 2) a protein expression unit comprising a DNA coding for a protein having target activity and a DNA fragment comprising a promoter and a terminator that function in the anaerobic microorganism, (3) the therapeutic agent according to (2), wherein the protein having target activity is a protein having therapeutic activity for a disease that is in an anaerobic environment, (4) the therapeutic agent according to (3), wherein the protein having therapeutic activity for a disease that is in an anaerobic environment is (a) a protein having an antitumor activity or (b) a protein having an activity of converting an antitumor substance precursor into an antitumor substance, (5) the therapeutic agent according to (4), wherein the protein having therapeutic activity for a disease that is in an anaerobic environment is (b) a protein having activity in converting an antitumor substance precursor into an antitumor substance, (6) the therapeutic agent according to (1), wherein the anaerobic microorganism is selected from the group consisting of *Bifidobacterium, Lactobacillus, Enterococcus, Streptococcus*, and *Clostridium*, (7) the therapeutic agent according to (6), wherein the anaerobic microorganism is *Bifidobacterium*, (8) the therapeutic agent according to (7), wherein the *Bifidobacterium* is selected from the group consisting of *B. adolescentis, B. animalis, B. infantis, B. thermophilum, B. pseudolongum, B. bifidum, B. breve*, and *B. longum*, (9) the therapeutic agent according to (8), wherein the *Bifidobacterium* is *B. longum*,

(10) the therapeutic agent according to (9), wherein the *Bifidobacterium* is *B. longum* 105-A/pBifiCD (NPMD Accession Number NITE BP-491),

(11) the therapeutic agent according to (5), wherein the protein having an activity of converting an antitumor substance precursor into an antitumor substance is selected from the group consisting of cytosine deaminase, nitroreductase, and b-glucuronidase,

(12) the therapeutic agent according to (11), wherein the protein having an activity of converting an antitumor substance precursor into an antitumor substance is cytosine deaminase,

(13) the therapeutic agent according to (1), wherein the colonization and proliferation enhancer for the anaerobic microorganism is at least one selected from the group consisting of arabinose, xylose, galactose, glucose, maltose, lactose, melibiose, melezitose, raffinose, and lactulose,

(14) the therapeutic agent according to (13), wherein the colonization and proliferation enhancer for the anaerobic microorganism is glucose or maltose,

(15) the therapeutic agent according to (14), wherein the colonization and proliferation enhancer for the anaerobic microorganism is maltose,

(16) a colonization and proliferation enhancer for an anaerobic microorganism for the treatment of an anaerobic disease, comprising as an active component at least one selected from the group consisting of arabinose, xylose, galactose, glucose, maltose, lactose, melibiose, melezitose, raffinose, and lactulose,

(17) the colonization and proliferation enhancer for the anaerobic microorganism for the treatment of an anaerobic disease according to (16), wherein the active component is glucose or maltose,

(18) the colonization and proliferation enhancer for the anaerobic microorganism for the treatment of an anaerobic disease according to (17), wherein the active component is maltose,

(19) the therapeutic agent according to (1), wherein the pharmaceutical composition comprising as an active component a colonization and proliferation enhancer for the anaerobic microorganism is a preparation for intravenous administration,

(20) the therapeutic agent according to (19), wherein the active component is glucose or maltose,

(21) the therapeutic agent according to (5), further comprising a pharmaceutical composition comprising as an active component an antitumor substance precursor that is converted into an antitumor substance by (b) a protein having an activity of converting an antitumor substance precursor into an antitumor substance, and

(22) the therapeutic agent according to (21), wherein the antitumor substance precursor is 5-fluorocytosine.

Advantageous Effects of Invention

The therapeutic agent for an anaerobic disease of the present invention has no risk that a recombinant gene is replicated in *E. coli*, and it is extremely safe in the environmental point of view and in actual treatment. Furthermore, the colonization and proliferation enhancer for a transformed anaerobic microorganism of the present invention improves the therapeutic effect by promoting specific colonization and proliferation of a transformed anaerobic microorganism for the treatment of an anaerobic disease at a disease site, and enables the dose of the microorganism to be reduced. An anaerobic disease therapeutic agent in which a pharmaceutical composition containing the transformed anaerobic microorganism for the treatment of an anaerobic disease of the present invention as an active component and a pharmaceutical composition containing the anaerobic microorganism colonization and proliferation enhancer of the present invention as an active component are combined is promising as a safe and excellent therapeutic agent that can markedly improve the therapeutic effect of the transformed anaerobic microorganism and enable the dose of the transformed anaerobic microorganism to be reduced.

DESCRIPTION OF EMBODIMENTS

Figure 1:
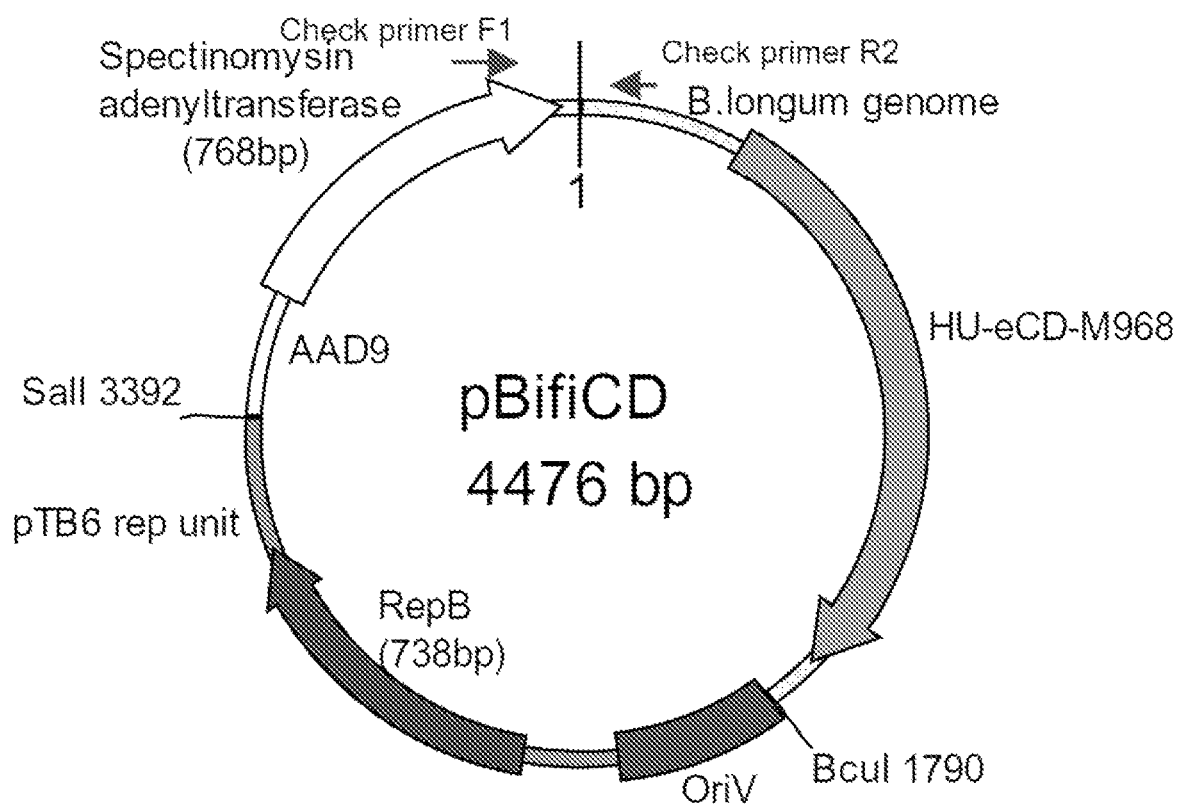
FIG. 1 is a diagram showing a map of the plasmid 'pBifiCD'.

The present invention provides a therapeutic agent an anaerobic disease that, in one embodiment, comprises in combination a pharmaceutical composition comprising as an active component a transformed anaerobic microorganism transformed with an expression vector that functions in the anaerobic microorganism and does not comprise a plasmid replication unit that functions in *E. coli*, and a pharmaceutical composition comprising as an active component a colonization and proliferation enhancer for the transformed anaerobic microorganism at an anaerobic disease site.

The 'therapeutic agent comprising in combination pharmaceutical compositions' referred to in the present specification means either a therapeutic agent that is a novel pharmaceutical composition produced by mixing at least two types of pharmaceutical compositions or a disease therapeutic agent comprising at least two types of pharmaceutical compositions that are used in combination in treatment. When at least two types of pharmaceutical compositions are used in combination, the pharmaceutical compositions may be used at the same time or may be used separately at a fixed interval.

The transformed anaerobic microorganism for the treatment of an anaerobic disease of the present invention is an anaerobic microorganism transformed with an expression vector, which is a plasmid vector that functions in an anaerobic bacterium, in particular, an enterobacterium other than *E. coli*, such as *Bifidobacterium, Lactobacillus, Enterococcus, Streptococcus*, or *Clostridium*. The expression vector of the present invention does not contain a plasmid replication unit that functions in a bacterium, particularly *E. coli*, other than the transformed bacterium.

The transformed anaerobic microorganisms for the treatment of an anaerobic disease that have been reported so far are transformed by shuttle vectors that function in both *E. coli* and a transformed bacterium, and none of them was transformed with a expression vector that functions only in a non-*E. coli* transformant. Therefore, the introduced gene can be horizontally transferred to a pathogenic bacterium or an aerobic or facultative anaerobic bacterium other than the transformed anaerobic bacterium, and the environmental risk and risks in actual treatment are concerned.

On the other hand, the transformed anaerobic microorganism of the present invention has been transformed with an expression vector that does not contain a plasmid replication unit that functions in a bacterium other than the transformant, particularly *E. coli*, and even if horizontal transfer to *E. coli* occurs, there is no possibility of replication in *E. coli*, and it is very safe in terms of the environment and in actual treatment.

More specifically, the expression vector used in transformation of the anaerobic microorganism for the treatment of an anaerobic disease of the present invention is characterized in that, for example, the expression vector consists essentially of (1) a plasmid replication unit that functions in an anaerobic microorganism other than *E. coli*, and (2) a protein expression unit consisting essentially of a DNA coding for a protein having target activity and a DNA fragment containing a promoter and a terminator that function in the anaerobic microorganism, and that the expression vector does not comprise a plasmid replication unit that functions in a bacterium other than the transformant, particularly *E. coli*.

As the plasmid replication unit, which functions in an anaerobic microorganism other than *E. coli*, possessed by the expression vector, any plasmid replication unit may be used as long as it functions in an anaerobic microorganism other than *E. coli*, for example, in an enterobacterium such as *Bifidobacterium, Lactobacillus, Enterococcus, Streptococcus*, or *Clostridium*, and does not function in an anaerobic microorganism other than the transformed bacterium; examples thereof include a plasmid replication unit that functions in an anaerobic microorganism other than *E. coli*, for example, in *Bifidobacterium*, and specific examples thereof include a pTB6 rep unit formed from an OriV region and a RepB gene that function in *Bifidobacterium*, and a single-nucleotide polymorphism thereof.

Furthermore, as the promoter and the terminator of the protein expression unit of the expression vector, any promoter and terminator may be used as long as they function in an anaerobic microorganism, for example, in an enterobacterium such as *Bifidobacterium, Lactobacillus, Enterococcus, Streptococcus*, or *Clostridium*; examples thereof include a promoter and a terminator of a gene coding for a histone-like DNA-binding protein that functions in an anaerobic microorganism, for example, a promoter and terminator DNA of a gene coding for *Bifidobacterium*-derived histone-like DNA-binding protein or a single-nucleotide polymorphism thereof.

The expression vector of the present invention may further comprise a selection marker activity gene unit. The selection marker activity is not particularly limited as long as it is capable of selecting an anaerobic microorganism transformed by the plasmid vector of the present invention; examples thereof include a drug resistance marker such as spectinomycin resistance, ampicillin resistance, tetracycline resistance, neomycin resistance, or kanamycin resistance, and auxotrophy, and spectinomycin resistance is preferable.

Examples of the selection marker activity gene unit include a DNA comprising a DNA coding for a protein exhibiting spectinomycin resistance activity or a single-nucleotide variant thereof and a promoter sequence thereof, for example, DNA coding for *enterococcus faecalis*-derived spectinomycin adenyltransferase (hereinafter, called AAD9 cassette) and a single-nucleotide polymorphism thereof.

The 'single-nucleotide variant' referred to in the present invention means a single-nucleotide polymorphism in which a nucleotide of at least one site has been altered (hereinafter, called a SNP), and includes not only a SNP at only one site but also SNPs at a plurality of sites.

As a gene inserted into a protein expression unit of the expression vector, any gene may be used as long as it expresses a protein having therapeutic activity for a disease that is in an anaerobic environment; for example, when the anaerobic disease therapeutic agent of the present invention is used as a malignant tumor therapeutic agent, a protein having an antitumor activity or a protein having an activity of converting an antitumor substance precursor into an antitumor substance, and as long as the gene not being DNA that inhibits transformation such as giant DNA (at least about 10 kb) or DNA that is toxic to recipient cells.

The protein having antitumor activity expressed by the gene includes, for example, a cytokine, and specific examples of the cytokine include interferons (IFN)-alpha, beta, and gamma, granulocyte macrophage colony stimulating factor (GM-CSF), interleukins (IL)-1 alpha, 1 beta, 2, 3, 4, 6, 7, 10, 12, 13, 15, and 18, tumor necrosis factor (TNF)-alpha, lymphotoxin (LT)-beta, granulocyte colony stimulating factor (G-CSF), macrophage colony stimulating factor (M-CSF), macrophage migration inhibition factor (MIF), leukemia inhibitory factor (LIF), T-cell activation costimulatory factors B7 (CD80) and B7-2 (CD86), KIT ligand, and oncostatin M. Furthermore, examples include angiogenesis suppressing substances such as endostatin, angiostatin, and kringles 1, 2, 3, 4, and 5.

The sequences of these proteins are known for various organisms, and by utilizing a known technique such as a PCR method based on the sequence information it is possible to obtain a DNA coding for a protein having antitumor activity used in the present invention.

Furthermore, examples of the protein having an activity of converting an antitumor substance precursor into an antitumor substance include cytosine deaminase (hereinafter, called CD), which is an enzyme that converts 5-fluorocytosine (hereinafter, called 5-FC) into the antitumor-active substance 5-fluorouracil (hereinafter, called 5-FU), nitroreductase, which is an enzyme that converts 5-aziridino-2,4-dinitrobenzamide (hereinafter, called CB1945) into an antitumor-active alkylating agent, herpes simplex virus 1 type thymidine kinase (hereinafter, called HSV1-TK), which is an enzyme that converts ganciclovir into an antitumor-active metabolite, and beta-glucuronidase, which is an enzyme that converts a glucuronidated antitumor-active substance into an antitumor active substance, and preferred examples thereof include CD, which is the enzyme that converts 5-FC into 5-FU.

As a DNA coding for such a CD, for example, that isolated from plasmid pAdex 1 CSCD (Riken Gene Bank RDB No. 1591), which contains a DNA coding for *E. coli*-derived CD, or plasmid pMK116, which similarly contains a DNA coding for *E. coli*-derived CD, may be used (D. A. Mead et al., Protein Engineering 1: 67-74 (1986)).

Furthermore, when the therapeutic agent for an anaerobic disease of the present invention is used as a therapeutic agent for an ischemic disease, a gene inserted into a protein expression unit of the expression vector of the present invention may include a protein having angiogenic promoting activity, which is useful for treatment of an ischemic disease. Specific examples include fibroblast growth factor 2 (FGF2), endothelial cell growth factor (ECGF), vascular endothelial growth factor (VEGF), and hepatocyte growth factor (HGF).

Similarly, the sequences of these proteins are known for various organisms, and by utilizing a known technique such as a PCR method based on the sequence information it is possible to obtain a DNA coding for a protein having angiogenic promoting activity used in the present invention.

The expression vector used for transformation of the anaerobic microorganism for the treatment of an anaerobic disease of the present invention includes any plasmid as long as the plasmid comprises, for example, a plasmid replication unit that functions in an anaerobic microorganism other than *E. coli*, and a protein expression unit comprising a DNA coding for a protein having target activity and a DNA fragment comprising a promoter and a terminator that function in the anaerobic microorganism, and when transforming an anaerobic microorganism the plasmid functions within this anaerobic microorganism, but the plasmid does not contain a plasmid replication unit that functions in a bacterium other than the transformed bacterium, particularly *E. coli*.

Examples thereof include those constructed by introducing, into the shuttle plasmids pBLES100 (Matsumura et al., Biosci. Biotechnol. Biochem., 61, 1211-1212 (1997)), pAV001 (WO 2006-57289), pBRASTA101 (Tanaka et al., Biosci. Biotechnol. Biochem., 69(2): 422-425 (2005)), pDG7, pEBM3, pECM2, pLP825, etc. (Alessandra Argnani et al., Microbiology, 142: 109-114 (1996)), which have been reported in the publications, a protein expression unit comprising a DNA coding for a given protein having target activity and a DNA fragment comprising a promoter and a terminator that function in the anaerobic microorganism, and removing a plasmid replication unit that functions in *E. coli*.

Other examples thereof include the shuttle plasmid constructed by recombining a protein expression unit inserted into the plasmid such as pNTR500F, pCD540FT, etc. (U.S. Pat. Nos. 6,416,754 and 6,652,849, and US Patent Application Publication 2003/0103952), pBLES100-S-eCD (JP A 2002-97144), pAV001-HU-eCD-M968 (WO 2007-136107), with another given protein expression unit, and further removing therefrom a plasmid replication unit that functions in *E. coli*.

Specific examples of the expression vector of the present invention include a vector comprising a pTB6 rep unit comprising a RepB gene and an OriV region that function in *Bifidobacterium* as the plasmid replication unit that functions in an anaerobic microorganism other than *E. coli*, and comprising a promoter and a terminator of a gene coding for *Bifidobacterium*-derived histone-like DNA-binding protein as the DNA fragment comprising the promoter and the terminator that function in the anaerobic microorganism, and comprising a DNA coding for the CD enzyme that converts 5-FC into 5-FU as the DNA coding for the protein having target activity, and comprising a DNA (AAD9 cassette) that codes for *Enterococcus faecalis*-derived spectinomycin adenyltransferase as the selection marker activity gene unit.

More specific examples thereof include pBifiCD, which is represented by the nucleotide sequence of SEQ ID NO:1.

The expression vector used in transformation of the anaerobic microorganism for the treatment of an anaerobic disease of the present invention may be constructed in accordance with the description in, for example, U.S. provisional application No. 61/124,528.

Accordingly, the expression vector of the present invention may be constructed by (1) constructing a plasmid comprising an origin of replication of *E. coli*, for example pUC ori, and optionally a selection marker activity gene unit, for example an AAD9 cassette (hereinafter, called a selection marker plasmid) (Step 1), (2) preparing a linear plasmid of the selection marker plasmid, ligating it with a promoter and a terminator such as, for example, a promoter and a terminator of a gene coding for *Bifidobacterium*-derived histone-like DNA-binding protein, and (a) a protein having antitumor activity or (b) a protein having an activity of converting an antitumor substance precursor into an antitumor substance such as, for example, a fragment comprising a CD (hereinafter, called a protein expression unit), to construct a plasmid having a selection marker activity gene unit and a protein expression unit (hereinafter, called a selection marker-active protein plasmid) (Step 2), (3) preparing a linear plasmid of this selection marker-active protein plasmid, ligating it with a plasmid replication unit that functions in an anaerobic microorganism other than *E. coli* such as, for example, a DNA fragment of a pTB6 rep unit formed from a RepB gene and an OriV region that function in *Bifidobacterium* (hereinafter, called a plasmid replication unit), to construct a plasmid having an *E. coli* replication initiation site and a selection marker activity gene unit, a protein expression unit, and a plasmid replication unit (hereinafter, called a shuttle plasmid) (Step 3), and (4) removing the *E. coli* replication initiation site from the shuttle plasmid (hereinafter, called Step 4).

The procedure of each step may be carried out in accordance with a known method described in the literature.

The expression vector of the present invention may also be constructed by inserting, by a standard method, a protein expression unit comprising a DNA coding for a given protein having target activity and a DNA fragment containing a promoter and a terminator that function in the anaerobic microorganism into the above-mentioned various types of shuttle plasmids such as the shuttle plasmids pBLES100 (Matsumura et al., Biosci. Biotechnol. Biochem., 61, 1211-1212 (1997)), pAV001 (WO 2006-57289), pBRASTA101 (Tanaka et al., Biosci. Biotechnol. Biochem., 69(2): 422-425 (2005)), pDG7, pEBM3, pECM2, pLP825, etc. (Alessandra Argnani et al., Microbiology, 142: 109-114 (1996)) and pNTR500F, pCD540FT, etc. (U.S. Pat. Nos. 6,416,754 and 6,652,849, and US Patent Application Publication 2003/0103952), followed by similarly removing a plasmid replication unit that functions in *E. coli* by a standard method.

Furthermore, in the same manner as for the above plasmid pBifiCD of the present invention in which the pUC ori, which is the fragment containing the *E. coli* origin of replication, is removed from the plasmid pAV001-HU-eCD-M968 (WO 2007-136107), the expression vector of the present invention may also be constructed by removing a plasmid replication unit that functions in *E. coli* from the plasmids pNTR500F, pCD540FT (U.S. Pat. Nos. 6,416,754 and 6,652,849, and US Patent Application Publication 2003/0103952), pBLES100-S-eCD (JP A 2002-97144), etc.

Moreover, the expression vector of the present invention may also be constructed by recombining a protein expression unit inserted into the plasmids pNTR500F, pCD540FT (U.S. Pat. Nos. 6,416,754 and 6,652,849, and US Patent Application Publication 2003/0103952), pBLES100-S-eCD (JP A 2002-97144), pAV001-HU-eCD-M968 (WO 2007-136107), etc. with another given protein expression unit, and then removing therefrom a plasmid replication unit that functions in *E. coli*.

The transformed anaerobic microorganism for the treatment of an anaerobic disease of the present invention may be constructed by transforming a given anaerobic microorganism that is to be transformed in accordance with a known genetic engineering method using the above-mentioned expression vector.

Since the transformed anaerobic microorganism for the treatment of an anaerobic disease of the present invention is used in an agent for treating an anaerobic disease such as a solid tumor, it is essential for this anaerobic microorganism to be obligately anaerobic and nonpathogenic; pathogenic bacteria such as *Clostridium* or *Salmonella* may be used if they are made nonpathogenic, and a facultative anaerobic bacterium such as a *lactobacillus* may be used if it has been mutated to be obligately anaerobic.

Preferred examples include nonpathogenic anaerobic bacteria; nonpathogenic enterobacteria are more preferable, and among them bifidobacteria are the most preferable.

Examples of the bifidobacteria include *B. adolescentis*, *B. animalis*, *B. infantis*, *B. thermophilum*, *B. pseudolongum*, *B. bifidum*, *B. breve*, and *B. longum*, and *B. longum* is the most preferable.

These bacteria are either commercially available or readily available from a depository institution. For example, *B. longum* ATCC-15707, *B. bifidum* ATCC-11863, *B. infantis* ATCC-15697, etc. may be readily obtained from ATCC (The American Type Culture Collection).

The strain of each bacterium is not particularly limited, and examples of the strain of *B. longum* include *B. longum* 105-A strain, *B. longum* aE-194b strain, *B. longum* bs-601 strain, and *B. longum* M101-2 strain, and among them *B. longum* 105-A strain is preferable.

Examples of the strain of *B. breve* include *B. breve* standard strain (Japan Collection of Microorganisms (JCM) 1192), *B. breve* aS-1 strain, and *B. breve* 1-53-8W strain, and among them *B. breve* standard strain and *B. breve* aS-1 strain are preferable.

Examples of the strain of *B. infantis* include *B. infantis* standard strain (JCM1222) and *B. infantis* I-10-5 strain, and among them *B. infantis* standard strain and *B. infantis* I-10-5 strain are preferable.

Furthermore, examples of a strain of *B. lactentis* include *B. lactentis* standard strain (JCM1220).

The transformed anaerobic microorganism of the present invention is not particularly limited as long as it is capable of growing in a tissue that is in an anaerobic environment and expressing a protein having target activity and, moreover, having no risk of horizontal transfer of the retained expression vector to a bacterium other than the transformed bacterium, in particular to a pathogenic, or aerobic or facultative anaerobic microorganism.

Preferred examples of the transformed anaerobic microorganism of the present invention include a transformed anaerobic microorganism that is capable of growing in a tumor tissue that is in an anaerobic environment and expressing a protein having an activity of converting an antitumor substance precursor into an antitumor substance. More preferred examples thereof include a gene transporter formed from *Bifidobacterium* that is capable of growing in a tumor tissue that is in an anaerobic environment and express CD, which is an enzyme that converts 5-FC into 5-FU, and particularly preferred examples thereof include *B. longum* 105-A strain transformed by pBifiCD (*B. longum* 105-A/pBifiCD; NPMD Accession Number NITE BP-491).

The gene transporter of the present invention may be constructed in accordance with a method described in a commercial experimental textbook such as, for example, Gene Manual (Kodansha), Gene Manipulation Experimental Method, Ed. by Yasuyuki Takagi (Kodansha), Molecular Cloning, Cold Spring Harbor Laboratory (1982), Molecular Cloning 2nd Edition, Cold Spring Harbor Laboratory (1989), or Methods in Enzymol., 194 (1991).

The transformed anaerobic microorganism of the present invention exhibits a better therapeutic effect for an anaerobic disease by using it in combination with a colonization and proliferation enhancer for promoting colonization and proliferation of the microorganism in target body tissue.

Any anaerobic microorganism colonization and proliferation enhancer can be used in the present invention, as long as it can improve the colonization and proliferation of the transformed anaerobic microorganism of the present invention specifically at an anaerobic disease site, as long as it is safe and can be administered intravenously. Examples thereof include saccharides such as arabinose, xylose, galactose, glucose, maltose, lactose, melibiose, melezitose, raffinose, and lactulose.

Among them, glucose, lactulose, and maltose are preferable, and maltose is the most preferable.

The pharmaceutical composition comprising as an active component the transformed anaerobic microorganism of the present invention is not particularly limited as long as it comprises the transformed anaerobic microorganism of the present invention. Moreover, it may comprise two or more of the transformed anaerobic microorganism of the present invention. Furthermore, the pharmaceutical composition or the anaerobic disease therapeutic agent of the present invention may be used in combination with a pharmaceutical composition or a therapeutic agent that contains, other than the gene transporter of the present invention, a compound exhibiting a therapeutic effect on the anaerobic disease.

Examples of the form of the pharmaceutical composition for the treatment of an anaerobic disease containing as an active component the transformed anaerobic microorganism of the present invention include a liquid agent or a solid preparation containing the transformed anaerobic microorganism. The liquid agent may be produced by purifying a culture fluid of the transformed anaerobic microorganism of the present invention, adding thereto as required an appropriate physiological saline, fluid replacement, or medicinal additive, and filling an ampoule, vial, etc. therewith. The solid preparation may be produced by adding an appropriate protectant to a liquid agent, filling an ampoule, vial, etc. therewith, and then lyophilizing or L-drying, or by adding an appropriate protectant to a liquid agent, lyophilizing or L-drying this, and then filling an ampoule, vial, etc. therewith.

With regard to a method for administering a pharmaceutical composition containing as an active component the transformed anaerobic microorganism of the present invention, both oral administration and parenteral administration are possible, but parenteral administration is preferable and, for example, intravenous injection, subcutaneous injection, local infusion, or intracerebroventricular administration can be carried out, and intravenous injection is the most preferable.

The dose of the transformed anaerobic microorganism for the treatment of an anaerobic disease of the present invention is not particularly limited as long as it is an amount sufficient for colonizing an anaerobic disease site and growing to express an effective therapeutic dose of an active protein, but the dose is preferably as small as possible from the viewpoint of alleviating the burden on a patient during administration as much as possible.

The dose of the transformed anaerobic microorganism for the treatment of an anaerobic disease when used in actual treatment is appropriately selected depending on the severity of a disease, and the body weight, age or gender of a patient, and may be increased or decreased as appropriate depending on the degree of improvement. For example, the dose is appropriately set depending on the effective therapeutic dose of active protein produced by the anaerobic microorganism used, the amount of the active protein produced by the anaerobic microorganism used, etc.

Specifically, in the case of intravenous administration, in order to avoid a risk such as an embolization due to a mass of bacteria, it is preferable to use the injection at a concentration as low as possible, divide the injection into a plurality of injections, or dilute the injection with an appropriate transfusion liquid and administer by continuous infusion. For example, in the case of an adult, $10^6$ to $10^{12}$ cfu per kg body weight of the cells of the transformed anaerobic microorganism are administered once to a plurality of times per day, and successively or at intervals as appropriate for 1 day to a plurality of days. More specifically, 1 to 1000 mL per adult of a preparation containing $10^4$ to $10^{10}$ cfu/mL of the cells of the transformed anaerobic microorganism is administered directly or by diluting with an appropriate fluid replacement, and preferably dividing it into 1 to a plurality of times a day for 1 to a plurality of days successively.

Furthermore, in the case of local administration involving direct administration to diseased tissue, since it is necessary that the bacterial cells colonize and proliferate in the entire diseased tissue as much as possible, it is desirable to administer a high concentration injection is desirably administered at a plurality of positions of the diseased tissue. For example, in the case of an adult, $10^6$ to $10^{12}$ cfu per kg body weight of the cells of the anaerobic microorganism of the present invention are administered once or a plurality of times a day, and successively or at intervals as appropriate for 1 day to a plurality of days as necessary. More specifically, 1 to 1000 mL per adult of a preparation containing $10^4$ to $10^{10}$ cfu/mL of the cells of the anaerobic microorganism of the present invention is administered directly plurality of times a day for 1 to a plurality of successive days as necessary.

When it is observed that the bacteria in the diseased tissue have disappeared during the treatment period, the treatment is first suspended, and then bacteria are administered again in the same manner as above.

Examples of a pharmaceutical composition comprising as an active component the anaerobic microorganism colonization and proliferation enhancer of the present invention include a liquid agent or a solid preparation comprising the anaerobic microorganism colonization and proliferation enhancer. The liquid agent may be produced by dissolving the anaerobic microorganism colonization and proliferation enhancer in water for injection, adding thereto as necessary an appropriate pharmaceutical additive such as a buffer agent, an isotonizing agent, a stabilizer, or a pH adjusting agent, further sterilizing, and then charging into a bag or an infusion bottle. Furthermore, the solid preparation may be produced by mixing the anaerobic microorganism colonization and proliferation enhancer with an appropriate pharmaceutical additive such as a buffer agent, an isotonizing agent, a stabilizer, or a pH adjusting agent. When administering such a solid preparation, it is administered by dissolving it in sterilized water for injection, physiological saline, etc.

As a method for administering the pharmaceutical composition of the anaerobic microorganism colonization and proliferation enhancer of the present invention, intravenous administration is the most preferable, but it may be carried out as necessary by subcutaneous injection, local infusion, intracerebroventricular administration, etc., and oral administration may also be carried out.

The dose of the anaerobic microorganism colonization and proliferation enhancer of the present invention is not particularly limited as long as it is an amount that enables the transformed anaerobic microorganism of the present invention to specifically colonize an anaerobic disease site, proliferate to an effective therapeutic amount, and be continuously present during the treatment period until completion, but it is preferably an amount that has as little effect as possible on a patient or diseased tissue.

The dose used in actual treatment is appropriately selected depending on the body weight, age or gender of a patient, and may be increased or decreased as appropriate depending on the dose of the transformed anaerobic microorganism for the treatment of an anaerobic disease of the present invention.

Specifically, for example, when an anaerobic microorganism colonization and proliferation enhancer containing maltose as an active component is used for an adult, a 10% maltose solution for intravenous administration is administered at 3 to 20 mL per kg body weight once a day, and preferably at 5 to 10 mL per kg body weight once a day. More specifically, a 10% maltose solution preparation for intravenous administration is administered at 200 to 600 mL per adult once a day continuously during the treatment period.

The anaerobic microorganism colonization and proliferation enhancer of the present invention may be administered as an infusion liquid for diluting bacteria when the transformed anaerobic microorganism of the present invention is administered.

Moreover, the pharmaceutical composition or the therapeutic agent for an anaerobic disease of the present invention may contain additional components other than the transformed anaerobic microorganism or the anaerobic microorganism colonization and proliferation enhancer of the present invention as long as the effect of the present invention is not impaired. Examples of such additional components include a pharmaceutically acceptable support, an excipient, and a diluent.

When the transformed anaerobic microorganism of the present invention is an anaerobic bacterium into which is introduced a gene that can express a protein having an activity of converting an antitumor substance precursor into an antitumor substance, the pharmaceutical composition or the therapeutic agent for an anaerobic disease comprising the transformed anaerobic microorganism for the treatment of an anaerobic disease as an active component is used in a combination with an amount of an antitumor substance precursor that can be converted into an effective amount of an antitumor substance by the protein expressed by the transformed anaerobic microorganism.

This antitumor substance precursor may be contained in the pharmaceutical composition or the therapeutic agent for an anaerobic disease containing as an active component the transformed anaerobic microorganism of the present invention, but it is preferable to use a pharmaceutical composition containing the antitumor substance precursor in combination with a pharmaceutical composition or a therapeutic agent for an anaerobic disease containing the transformed anaerobic microorganism for the treatment of an anaerobic disease of the present invention as an active component.

The antitumor substance precursor used in the present invention is not particularly limited as long as it has few side effects on normal tissue in the precursor (prodrug) state and has a high therapeutic effect on the treatment target for an anaerobic disease after being converted into an antitumor substance, and examples thereof include 5-FC, which is a prodrug of 5-FU, CB 1945, which is converted into an antitumor-active alkylating agent, ganciclovir, which is converted into an antitumor-active metabolite, and a glucuronidated antitumor-active substance.

Accordingly, when the pharmaceutical composition or the therapeutic agent for an anaerobic disease of the present invention is used in combination with an antitumor substance precursor, the method for administering the pharmaceutical composition or the therapeutic agent for an anaerobic disease of the present invention may be the same as or different from the method for administering the pharmaceutical composition containing the antitumor substance precursor, and these administrations may be carried out at the same time or at separate times; administration of the pharmaceutical composition containing the antitumor substance precursor is preferably carried out after allowing a sufficient time for the transformed anaerobic microorganism of the present invention to grow on tumor cells after the pharmaceutical composition or the therapeutic agent for an anaerobic disease of the present invention is administered.

Furthermore, when the pharmaceutical composition or the therapeutic agent for an anaerobic disease of the present invention is used in combination with an antitumor substance precursor, since the transformed anaerobic microorganism for the treatment of an anaerobic disease colonizes and proliferates only in the tumor tissue that is in an anaerobic environment and locally produces an active protein there, compared with a method for treating a solid tumor using a normal antitumor substance precursor, side effects can be greatly suppressed, and the dose of the antitumor substance precursor can be set in a wide range.

The dose of the antitumor substance precursor may be selected appropriately according to the proliferation rate in tumor tissue of the transformed anaerobic microorganism used in combination and the efficiency of converting the antitumor substance precursor into the antitumor substance. In the same way as for the dose of the gene transporter, it may be selected as appropriate according to the severity of a disease, and the body weight, age or gender of a patient, and may be increased or decreased as appropriate according to the degree of improvement.

For example, in actual treatment, the dose is set appropriately depending on the type of the antitumor substance precursor used and the antitumor substance to be converted, the effective therapeutic dose of the antitumor substance converted from the antitumor substance precursor, the type of protein that is produced by the anaerobic microorganism used having an activity of converting the antitumor substance precursor into the antitumor substance, and the amount of active protein produced by the anaerobic microorganism used, etc.

Specifically, for example, when a CD expressing transformed anaerobic microorganism and the antitumor substance precursor 5-FC are administered in combination, after it is confirmed that the bacteria have colonized and grown in diseased tissue and the bacteria have disappeared in blood and normal tissue, 5-FC is administered at 1 to 100 mg/day per kg body weight of an adult once or a plurality of times a day successively during a treatment period. The administration method is preferably oral administration, but parenteral administration such as intravenous administration or anal administration may be carried out.

'In a combination of X and Y' referred to in the present invention includes both a case in which X and Y are each in different configurations and a case in which X and Y are in a single configuration (e.g. a configuration containing X and Y). When X and Y are in different configurations, X and Y may each further contain another component.

The pharmaceutical composition or the therapeutic agent for an anaerobic disease of the present invention may be applied to a disease that has an anaerobic environment, and preferably to various types of solid cancers. Examples of the solid cancer include large bowel cancer, brain tumor, head and neck cancer, breast cancer, lung cancer, esophageal cancer, stomach cancer, liver cancer, gallbladder cancer, bile duct cancer, pancreatic cancer, islet cell cancer, chorionic cancer, colonic cancer, renal cell cancer, adrenal cortex cancer, bladder cancer, testicular cancer, prostate cancer, testicular tumor, ovarian cancer, uterine cancer, thyroid cancer, malignant carcinoid tumor, skin cancer, malignant melanoma, osteosarcoma, soft tissue sarcoma, neuroblastoma, Wilms' tumor, retinoblastoma, melanoma, and squamous cancer.

Furthermore, examples of other diseases that are in an anaerobic environment include ischemic diseases such as cardiac infarction or arteriosclerosis obliterans, and lower limb ischemic diseases such as Buerger's disease.

EXAMPLES

The present invention is explained more specifically below by reference to Reference Examples and Examples, but the technical scope of the present invention is not limited to these Examples.

Production of *B. longum* Re-105A/pBifiCD (NITE BP-491) Frozen Preparation 2 mL of a culture liquid of *B. longum* Re-105A/pBifiCD produced by a method described in U.S. provisional application No. 61/124,528 was poured into 2 L of medium (APS-2S-2.5R medium) prepared by adding glucose, soy peptide (Hinute (Trademark) SMP), cysteine hydrochloride, potassium pantothenate, biotin, nicotinic acid, riboflavin, thiamine hydrochloride, ascorbic acid, sodium carbonate, p-aminobenzoic acid, thymidine, magnesium sulfate, manganese sulfate, sodium chloride, monopotassium phosphate, ferric chloride, etc., and anaerobic culturing was carried out at about 40 degree C. for 18 to 21 hours.

After culturing was completed, the bacterial liquid was purified by filtration using a filter equipped with an ultrafiltration membrane with a pore size of 0.8 micrometer (product number FS001K05, Pall Corporation), thus giving a purified bacterial liquid.

Water for injection was added to 100 g of glycerol to make the total amount 1 L, and this was filtered using a filter membrane with a pore size of 0.2 micrometer and then autoclaved at 121 degree C. for 20 minutes, thus giving a 10% glycerol solution.

An equal amount of the 10% glycerol solution was added to the purified bacterial liquid to give a 5% glycerol preparation solution, and 30 mL volume vial containers were each charged with 10 mL thereof, filled with sterile filtered nitrogen gas, and then sealed.

Subsequently, the vials were frozen using liquid nitrogen and stored within a deep freezer.

Assimilation of Various Types of Saccharides by *B. longum* Re-105A/pBifiCD (NITE BP-491)

Assimilation of various types of saccharides by *B. longum* Re-105A/pBifiCD (NITE BP-491) was confirmed using API 50 CH and API 20 A.

A colony was suspended in API 50 CH or API 20 A medium by a standard method, the turbidity was adjusted, a kit plate was then inoculated, culturing was carried out, and an assessment was made by color change after 24 hours and 48 hours of culturing. The assessment was carried out based on the results after 48 hours.

Each of the API 50 CH and API 20 A tests was carried out by two testers twice.

The API 20 A test was carried out for glycerol, arabinose, xylose, glucose, mannose, rhamnose, mannitol, sorbitol, salicin, cellobiose, maltose, lactose, sucrose, trehalose, melezitose, and raffinose, but since other saccharides were not included as test items, they were not tested.

An overall assessment was carried out based on the API 50 CH and API 20 A final assessments.

The API 50 CH and API 20 A final assessments were carried out based on the four test results for each (two tests by each of two testers).

When the API 50 CH and API 20 A final assessments were different, since API 20 A is a kit designed for *Bifidobacterium*, the API 20 A assessment was used, and with respect to test items other than those of API 20 A, the API 50 CH assessment was used.

The results were that L-arabinose, D-xylose, galactose, and glucose, which are monosaccharides, maltose, lactose, and melibiose, which are disaccharides, and melezitose and raffinose, which are trisaccharides, showed a positive, and ribose and fructose, which are monosaccharides, and sucrose, which is a disaccharide, showed a weak positive.

The test results are given in Table 1. In the table, (+) denotes positive, (−) denotes negative, and (w) denotes weak positive, and (v) and (wv) denote variability in the test results.

(NT) in the API 20 A column denotes the test not being carried out (non-tested item).

TABLE 1

Assimilation of various types of saccharides

| No. | Test substance | API 50 CH | API 20 A | Overall assessment |
|---|---|---|---|---|
| 1 | Glycerol | − | − | − |
| 2 | Erythritol | − | NT | − |
| 3 | d-Arabinose | − | NT | − |
| 4 | l-Arabinose | + | + | + |
| 5 | Ribose | wv | NT | wv |
| 6 | d-Xylose | + | + | + |
| 7 | l-Xylose | − | NT | − |
| 8 | Adonitol | − | NT | − |
| 9 | β-Methyl-d-xyloside | − | NT | − |
| 10 | Galactose | + | NT | + |
| 11 | Glucose | + | + | + |
| 12 | Fructose | wv | NT | wv |
| 13 | Mannose | − | v | v |
| 14 | Sorbose | − | NT | − |
| 15 | Rhamnose | − | − | − |
| 16 | Dulcitol | − | NT | − |
| 17 | Inositol | − | NT | − |
| 18 | Mannitol | − | − | − |
| 19 | Sorbitol | − | − | − |
| 20 | α-Methyl-d-mannoside | − | NT | − |
| 21 | α-Methyl-d-glucoside | − | NT | − |
| 22 | n-Acetylglucosamine | − | NT | − |
| 23 | Amygdalin | − | NT | − |
| 24 | Arbutin | − | NT | − |
| 25 | Esculin | − | NT | − |
| 26 | Salicin | − | − | − |
| 27 | Cellobiose | − | − | − |
| 28 | Maltose | + | + | + |
| 29 | Lactose | + | + | + |
| 30 | Melibiose | + | NT | + |
| 31 | Sucrose | − | wv | wv |
| 32 | Trehalose | − | − | − |
| 33 | Inulin | − | NT | − |
| 34 | Melezitose | + | + | + |
| 35 | Raffinose | + | + | + |
| 36 | Starch | − | NT | − |
| 37 | Glycogen | − | NT | − |
| 38 | Xylitol | − | NT | − |
| 39 | Gentiobiose | − | NT | − |
| 40 | d-Turanose | − | NT | − |
| 41 | d-Lyxose | − | NT | − |

TABLE 1-continued

Assimilation of various types of saccharides

| No. | Test substance | API 50 CH | API 20 A | Overall assessment |
|---|---|---|---|---|
| 42 | d-Tagatose | − | NT | − |
| 43 | d-Fucose | − | NT | − |
| 44 | l-Fucose | − | NT | − |
| 45 | d-Arabitol | − | NT | − |
| 46 | l-Arabitol | − | NT | − |
| 47 | Gluconate | − | NT | − |
| 48 | 2-Ketogluconate | − | NT | − |
| 49 | 5-Ketogluconate | − | NT | − |

Combined Use of *B. longum* Re-105A/pBifiCD and Glucose (1) Preparation of Tumor-Bearing Nude Mouse Human breast cancer cell line KPL-1 cells at $5 \times 10^5$ cells/mouse/0.2 mL were transplanted under the skin of the back side of the right forelimb of a nude mouse. The dimensions of the tumor (major diameter, minor diameter, thickness) were measured using calipers (Digimatic Caliper, CD-15PS, Mitutoyo, Kanagawa), and the tumor volume was determined from the equation below. Measurement of the tumor volume was carried out the day before administration of *B. longum* Re-105A/pBifiCD (Day-1) and 7 days after administration of *B. longum* Re-105A/pBifiCD (Day 7). Tumor volume $(mm^3)$=major diameter (mm)×minor diameter (mm)×thickness (mm)/2

(2) Administration of *B. longum* Re-105A/pBifiCD Frozen Preparation, 10% Glucose Solution, and Physiological Saline 22 tumor-bearing nude mice having a tumor volume of on the order of 80 to 150 $mm^3$ were selected from 61 KPL-1 tumor-bearing nude mice and divided into two groups (11 mice per group) with an equal level of tumor volume as a criterion. *B. longum* Re-105A/pBifiCD frozen preparation was intravenously administered to the mice of each group using a Myjector (29 G×½, TERUMO, Tokyo) 0.05 mL at a time 4 times a day (the interval between the 4 times of administration was 1 hour, and the preparation was left at room temperature during the administration period) (Day 0).

From the day after *B. longum* Re-105A/pBifiCD administration (Day 1), a 10% glucose solution was intraperitoneally administered to the first group [glucose (+) group] 1 mL at a time twice a day (A.M./P.M.) using an injection needle (25 G×1 R.B., TERMO), and the same amount was subsequently administered every day for 6 days until the day before tissue was removed (Day 6). Furthermore, physiological saline was administered to the second group [glucose (−) group] by the same method.

(3) Measurement of Number of Bacteria within Tumor for *B. Longum* Re-105A/pBifiCD (NITE BP-491)

7 days after administration of the preparation (Day 7), the mouse was euthanized, the tumor was removed, and the weight (g) was measured using an electronic balance (AB 104-S, METTLER TOLEDO, Tokyo). After the measurement, the tumor was finely cut into a minced state using scissors, the tumor was placed in a homogenizer tube (HOMOGENIZER, SANSYO, Tokyo), an anaerobic diluent was added thereto at a ratio of tumor weight (g):anaerobic diluent (mL)=1:9, and the mixture was ground using a homogenizer (NZ-1300, EYELA) at 300 rpm. The homogenized tumor liquid was diluted with an anaerobic diluent, and for each of the original liquid and the diluted liquid three BLFS plates were smeared with 100 micro litter thereof. The smeared BLFS plates were sealed in a sealed container together with a deoxygenating/carbon dioxide generating agent, and anaerobically cultured in an incubator at 37 degree C. for 3 days. After culturing, the number of colonies on the plate was counted, and the number of bacteria within the tumor was determined from a BLFS plate for which the number of colonies was within 30 to 300 (when there was no plate with a number of colonies in the above-mentioned range, a plate with a number of colonies that was the closest to the range was selected). The number of bacteria within the tumor was calculated from the equation below.

Method for Calculating Number of Bacteria within Tumor

Number of bacteria within tumor (cfu/g)=average number of colonies (n)×dilution ratio when homogenizing tumor (x)×dilution ratio at plating (y)×10(z)

(n): (P1+P2+P3)/3; P1, 2, and 3 are the numbers of colonies on each plate (x): {tumor weight (g)+amount of anaerobic diluent (mL)}/tumor weight (g)

(y): A: ×1 (original liquid), B: $\times 10^2$ ($10^2$ times dilution), C: $\times 10^4$ ($10^4$ times dilution), (z): a constant for converting the value to number of bacteria per g of tumor {because 100 micro litter (=0.1 g) of homogenate liquid is plated onto each plate}

Statistical Analysis

The experimental results thus obtained were expressed as an average value plus/minus standard deviation. SPSS (statistical analysis software, SPSS Inc., Tokyo) was used in testing the glucose (+) group and the glucose (−) group. The test results were taken as being significantly different for $p<0.05$.

(5) Results: Comparison of Colonization and Proliferation of Glucose (+) Group and Glucose (−) Group in Tumor Tissue In KPL-1 tumor-bearing nude mice having a tumor volume of on the order of 80 to 150 $mm^3$ there was colonization of *B. longum* Re-105A/pBifiCD in the tumor in 10 cases out of 11 mice for the glucose (+) group and 4 cases out of 11 mice for the glucose (−) group. From this result, a significant difference was observed for colonization of *B. longum* Re-105A/pBifiCD in the tumor between the glucose (+) group and the glucose (−) group (Fisher exact probability test: p=0.024). Furthermore, the average number of bacteria within the tumor for the mice of the groups where colonization was observed was $1.8 \times 10^6$ plus/minus $1.9 \times 10^6$ cfu/g (n=10) for the glucose (+) group and $1.1 \times 10^4$ plus/minus $1.6 \times 10^4$ cfu/g (n=4) for the glucose (−) group, and a significant difference was observed in proliferation within the tumor between the two groups (Mann-Whitney U-test; P=0.008).

From the above, it was confirmed that glucose exhibited an effect in promoting specific colonization of *B. longum* Re-105A/pBifiCD in tumor tissue and an effect in promoting proliferation in tumor tissue.

Use of *B. longum* Re-105A/pBifiCD and Maltose in Combination (1)

1) Preparation of Tumor-Bearing Nude Mouse and Measurement of Tumor Volume

Preparation of tumor-bearing nude mice and measurement of tumor volume were carried out in the same manner as in Example 1.

The number of cells transplanted was $5 \times 10^5$ cells/mouse, the volume transplanted (concentration of cell liquid) was 0.2 mL ($2.5 \times 10^6$ cells/mL), and the transplantation site was under the skin of the back side of the right forelimb.

(2) Grouping 42 animals with no abnormalities using general condition and change in weight as criteria were selected from tumor-bearing nude mice having a tumor volume of about 50 to 200 $mm^3$ on the day before administration of bacteria (Day-1), and they were divided into 7 groups by a stratified continuous randomization method so that the average tumor volumes were at an equal level.

(3) Administration of B. longum Re-105A/pBifiCD Frozen Preparation and 10% Maltose Solution The B. longum Re-105A/pBifiCD frozen preparation was thawed completely using a thermostat bath at 37 degree C. for 10 minutes immediately before use. The thawed bacterial preparation was dispersed by lightly tumble-mixing, and a predetermined quantity [0.2 mL×twice (AM/PM)/day; total 0.4 mL/mouse] was measured.

Administration was carried out once in the morning and once in the afternoon, and the administration in the afternoon was carried out after an interval of 4 hours from the administration in the morning (permissible time was within 30 minutes). The order of administration was from the youngest individual number for each group, and administration was carried out in order from group A to group H. Administration was carried out into a tail vein using a 26 G injection needle and a 1 mL polypropylene syringe.

In accordance with the group constitution shown in Table 2 below, maltose liquid (Otsuka Pharmaceutical Factory, Inc., 10% maltose injection) or physiological saline [1 mL×twice (AM/PM)/day; total 2 mL/mouse] was intraperitoneally administered (ip).

Intraperitoneal administration on Day 0 was carried out within 1 hour after tail vein administration for 6 mice in each group was completed in both morning and afternoon.

From Day 1 onward, administration was carried out once in the morning and afternoon, and the administration in the afternoon was carried out after an interval of 4 hours from the administration in the morning (permissible time was within 30 minutes).

TABLE 2

Group constitution

| Group | Agent administered | Administration period* | Autopsy day | Number of animals |
|---|---|---|---|---|
| A | 10% maltose (ip) | Day 0 | Day 1 | 6 |
| B | 10% maltose (ip) | Day 0 to Day 6 | Day 7 | 6 |
| C | 10% maltose (ip) | Day 0 to Day 13 | Day 14 | 6 |
| D | 10% maltose (ip) | Day 0 to Day 6 | Day 14 | 6 |
| F | Physiological saline (ip) | Day 0 | Day 1 | 6 |
| G | Physiological saline (ip) | Day 0 to Day 6 | Day 7 | 6 |
| H | Physiological saline (ip) | Day 0 to Day 13 | Day 14 | 6 |

*The day of administration of bacteria was defined as Day 0.

(4) Measurement of Number of Bacteria within Tumor and Liver

In accordance with the group constitution described in Table 2 of (3) above, mice were euthanized on Day 1, Day 7, and Day 14, the tumor and the liver were removed, and the weight (g) was measured using an electronic balance (AB204-S, METTLER TOLEDO, Tokyo).

The tissue removed was finely cut into a minced state using scissors and placed in a homogenizer tube (HOMOGENIZER, SANSYO, Tokyo), an anaerobic diluent was added thereto at a ratio of tissue weight (g):anaerobic diluent (mL)=1:9, and the mixture was ground using a homogenizer (NZ-1300, EYELA) at 300 rpm.

The homogenized tissue liquid was diluted with an anaerobic diluent, and for each of the original liquid and the diluted liquid three BLFS plates were smeared with 100 micro litter thereof. The smeared BLFS plates were sealed in a sealed container together with a deoxygenating/carbon dioxide generating agent, and anaerobically cultured in a thermostatic chamber at 37 degree C. for 3 days.

Furthermore, 100 micro litter of the B. longum Re-105A/pBifiCD frozen preparation was diluted $10^6$ times with an anaerobic diluent, and a BLFS plate smeared with 100 micro litter of the diluted liquid was cultured as a positive control at the same time in a sealed container.

After culturing, the number of colonies on the plate was counted, and the numbers of bacteria within the tumor and the liver were determined from BLFS plates for which the number of colonies was within 30 to 300. When there was no plate with a number of colonies in the above-mentioned range, a plate with a number of colonies that was the closest to the range was selected.

The number of bacteria within the tissue was calculated in the same manner as in Example 1 (3).

(5) Results 1: Comparison of Colonization in Tumor and Number of Bacteria within Tumor Between Maltose-Administered Group and Non-Maltose-Administered Group Colonization in the tumor and the number of bacteria within the tumor (mean value/median value) of the maltose-administered group and the non-maltose-administered group on the day after final administration of bacteria (Day 1), 7 days after administration (Day 7), and 14 days after administration (Day 14) are shown in Table 3 and Table 4.

TABLE 3

Number of bacteria within tumor of maltose-administered group

| | Group | | | |
|---|---|---|---|---|
| No. | A Administration period: Day 0 Autopsy day: Day 1 | B Day 0 to Day 6 Day 7 | C Day 0 to Day 13 Day 14 | D Day 0 to Day 6 Day 14 |
| 1 | $5.3 \times 10^5$ | $9.8 \times 10^1$ | $4.7 \times 10^7$ | $1.2 \times 10^7$ |
| 2 | $3.4 \times 10^5$ | $4.3 \times 10^5$ | $1.0 \times 10^6$ | $2.4 \times 10^5$ |
| 3 | $2.1 \times 10^6$ | $4.2 \times 10^7$ | $2.4 \times 10^7$ | $4.1 \times 10^4$ |
| 4 | $8.3 \times 10^5$ | N.D. | $1.4 \times 10^6$ | $3.7 \times 10^4$ |
| 5 | $5.1 \times 10^5$ | $3.7 \times 10^6$ | $3.5 \times 10^5$ | $1.8 \times 10^5$ |
| 6 | $4.0 \times 10^5$ | $1.0 \times 10^7$ | $1.6 \times 10^6$ | $8.6 \times 10^4$ |
| Mean | $7.9 \times 10^5$ | $1.1 \times 10^7$ | $1.3 \times 10^7$ | $2.1 \times 10^6$ |
| Median | $5.2 \times 10^5$ | $3.7 \times 10^6$ | $1.5 \times 10^6$ | $1.3 \times 10^5$ |

TABLE 4

Number of bacteria within tumor of non-maltose-administered group (physiological saline-administered group)

| | Group | | |
|---|---|---|---|
| No. | F Administration period: Day 0 Autopsy day: Day 1 | G Day 0 to Day 6 Day 7 | H Day 0 to Day 13 Day 14 |
| 1 | $7.2 \times 10^3$ | $2.0 \times 10^5$ | $2.5 \times 10^5$ |
| 2 | $1.4 \times 10^4$ | $3.3 \times 10^1$ | $3.3 \times 10^2$ |
| 3 | $1.5 \times 10^5$ | $7.1 \times 10^4$ | $6.6 \times 10^1$ |
| 4 | $1.4 \times 10^4$ | $2.5 \times 10^5$ | $1.6 \times 10^3$ |
| 5 | $4.2 \times 10^5$ | $2.0 \times 10^6$ | $2.2 \times 10^5$ |
| 6 | $8.0 \times 10^3$ | $1.7 \times 10^5$ | $2.8 \times 10^5$ |
| Mean | $1.0 \times 10^5$ | $4.5 \times 10^5$ | $1.3 \times 10^5$ |
| Median | $1.4 \times 10^4$ | $1.9 \times 10^5$ | $1.1 \times 10^5$ |

Comparison of Number of Bacteria within Tumor on Day 1

From the results of comparing the number of bacteria within a tumor between group A (maltose-administered group) and group F (non-maltose-administered group) using the median value as a criterion, there were more in group A than in group F, and there was a statistically significant difference (Mann-Whitney U-test; P=0.009).

From this it was confirmed that maltose exhibits an effect in promoting specific colonization of B. longum Re-105A/pBifiCD in tumor tissue.

Comparison of Number of Bacteria within Tumor on Day 7

From the results of comparing the number of bacteria within a tumor between group B (maltose-administered group) and group G (non-maltose-administered group) using the median value as a criterion, there were more in group B than in group G. From this it was confirmed that maltose exhibits an effect in promoting the proliferation of B. longum Re-105A/pBifiCD in tumor tissue.

Comparison of Number of Bacteria within Tumor on Day 14

From the results of comparing the number of bacteria within a tumor between group C (maltose-administered group) and group H (non-maltose-administered group) using the median value as a criterion, there were more in group A than in group F, and there was a statistically significant difference (Mann-Whitney U-test (Bonnferoni correction; significant if P<0.017); P=0.002).

On the other hand, the number of bacteria within a tumor of group D (group in which maltose administration was suspended from Day 7 onward) was at an equal level to group H, and there was no statistically significant difference (Mann-Whitney U-test (Bonnferoni correction; significant if P<0.017) P=0.589).

From this it was confirmed that maltose exhibits an effect in promoting the proliferation and an effect of maintaining the proliferation of B. longum Re-105A/pBifiCD in tumor tissue and, furthermore, it was confirmed that continuous administration is necessary for maintaining the proliferation.

(6) Results 2: Comparison of Colonization in Liver and Number of Bacteria in the Liver Between Maltose-Administered Group and Non-Maltose-Administered Group Colonization in the liver and the number of bacteria within the liver (mean value/median value) of the maltose-administered group and the non-maltose-administered group on the day after final administration of bacteria (Day 1), 7 days after administration (Day 7), and 14 days after administration (Day 14) are shown in Table 5 and Table 6.

TABLE 5

Number of bacteria within liver of maltose-administered group

| | Group | | | |
|---|---|---|---|---|
| No. | A<br>Administration<br>period: Day 0<br>Autopsy day:<br>Day 1 | B<br>Day 0 to<br>Day 6<br>Day 7 | C<br>Day 0 to<br>Day 13<br>Day 14 | D<br>Day 0 to<br>Day 6<br>Day 14 |
| 1 | $3.3 \times 10^3$ | N.D. | N.D. | N.D. |
| 2 | $2.9 \times 10^3$ | N.D. | N.D. | N.D. |
| 3 | $5.1 \times 10^2$ | N.D. | N.D. | N.D. |
| 4 | $3.5 \times 10^3$ | N.D. | N.D. | N.D. |
| 5 | $5.3 \times 10^2$ | N.D. | N.D. | N.D. |
| 6 | $9.4 \times 10^2$ | N.D. | N.D. | N.D. |
| Mean | $2.0 \times 10^3$ | N.D. | N.D. | N.D. |
| Median | $1.9 \times 10^3$ | N.D. | N.D. | N.D. |

TABLE 6

Number of bacteria within liver of non-maltose-administered group (physiological saline-administered group)

| | Group | | |
|---|---|---|---|
| No. | F<br>Administration<br>period: Day 0<br>Autopsy day: Day<br>1 | G<br>Day 0 to<br>Day 6<br>Day 7 | H<br>Day 0 to<br>Day 13<br>Day 14 |
| 1 | $8.0 \times 10^2$ | N.D. | N.D. |
| 2 | $3.3 \times 10^1$ | N.D. | N.D. |
| 3 | $8.5 \times 10^2$ | N.D. | N.D. |
| 4 | $2.6 \times 10^2$ | N.D. | N.D. |
| 5 | $4.6 \times 10^2$ | N.D. | N.D. |
| 6 | $2.6 \times 10^3$ | N.D. | N.D. |
| Mean | $8.3 \times 10^2$ | N.D. | N.D. |
| Median | $6.3 \times 10^2$ | N.D. | N.D. |

Comparison of number of bacteria in liver between maltose-administered group and non-maltose-administered group on Day 1, Day 7, and Day 14

On Day 1, bacteria were observed within the liver for both the maltose-administered group and the non-administered group, but on Day 7 and Day 14 bacteria were observed in neither of the groups.

From this it was confirmed that maltose does not affect the colonization and proliferation of B. longum Re-105A/pBifiCD in normal tissue.

Use of B. longum Re-105A/pBifiCD and Maltose in Combination (2)

(1) Culturing and Subculturing of Tumor Cells

Human stomach cancer cell line MKN45 cells were statically cultured using a $CO_2$ incubator set at 37 degree C. with 5% $CO_2$ (MCO-20AIC, Sanyo Electric Co., Ltd.) under humidifying conditions. Furthermore, subculturing was carried out by the following procedure when the cell density became confluent. The medium within the culture container was removed, and it was lightly rinsed using $Ca^{2+}$, $Mg^{2+}$-free Dulbecco's phosphate buffered saline (PBS(−), Lot No. 160708, Nissui Pharmaceutical Co., Ltd.). After PBS(−) was aspirated, small amounts sufficient for the cells to be immersed of 0.25% trypsin (Lot No. 6280J, Wako Pure Chemical Industries, Ltd.) and 0.02% EDTA (Lot No. SS054, Wako Pure Chemical Industries, Ltd.)-containing PBS(−) (trypsin/EDTA liquid) were added thereto and the mixture was allowed to stand within a $CO_2$ incubator.

After confirming that the cells had substantially peeled off from the bottom of the culture container when examined using a microscope, a growth medium was added. The cells were separated by pipetting, then transferred to a centrifugation tube, and centrifuged at about 1,000 rpm (180×g) for 5 minutes. The supernatant was removed, growth medium was added, and a culture container was inoculated with the cells. Subculturing of the cells was carried out every 3 or 4 days.

(2) Transplanting of Tumor Cells

The cells collected in (1) above were washed using PBS(−). The cells were suspended in an appropriate amount of PBS (−), part thereof was mixed with 0.4% trypan blue, and the number of cells and the viability were determined. The result was that the viability was 93%. The viable cell density was adjusted to $5 \times 10^7$ cells/mL using PBS(−). The cell suspension was stored under ice cooling until it was used for transplantation.

Transplantation was carried out under the skin of the right dosal area of an animal using a 1 mL syringe (Terumo Corp.) and a 26 G injection needle (Terumo Corp.).

Number of cells transplanted: $5\times10^6$ cells/0.1 mL/body (3) Grouping and Test Group Constitution Grouping After the tumor cells were transplanted, the major diameter and the minor diameter of the tumor were measured using calipers (CD-S20C, Mitutoyo), and the volume of the tumor was determined from the equation of (8) below. First, 'removal of individual by single variable' was carried out, and animals to be used in the experiment were selected. These animals had an average tumor volume of 221.5 mm$^3$. 'Blocked allocation by single variable' was carried out, and allocation was carried out so that the average value of the tumor volume was equal for each test group. This day was set as Day 0 (10 days after transplantation). As software, SAS System Release 8.2 (SAS Preclinical Package Version 5.0, SAS Institute Japan) was used.

Test Group Constitution

The test group constitution was as shown in Table 7.

TABLE 7

Test group constitution

| Group | Substance administered | Dose | Administration frequency (/day) | Administration day (day) | Number of animals |
|---|---|---|---|---|---|
| First group | Bacteria | — | — | — | 8 |
|  | 5-FC | — | — | — |  |
|  | Maltose | — | — | — |  |
| Second group | Bacteria | $1\times10^{10}$ (cfu/kg/day) | 1 | 1 to 3 | 8 |
|  | 5-FC | 750 (mg/kg/day) | 3 | 5 to 25, 26 |  |
|  | Maltose | 200 (mg/body/day) | 2 | 1 to 25 |  |
| Third group | Bacteria | $4\times10^{10}$ (cfu/kg/day) | 1 | 1 to 3 | 8 |
|  | 5-FC | 750 (mg/kg/day) | 3 | 5 to 25, 26 |  |
|  | Maltose | 200 (mg/body/day) | 2 | 1 to 25 |  |
| Fourth group | Bacteria | $4\times10^{10}$ (cfu/kg/day) | 1 | 1 to 3 | 8 |
|  | 5-FC | 750 (mg/kg/day) | 3 | 5 to 25, 26 |  |
|  | Maltose | — | 2* | 1 to 25 |  |

Note)
*For the fourth group, physiological saline was administered instead of maltose.

(4) Preparation of Administration Liquids

Preparation Method and Preparation Frequency for Bacteria (*B. Longum* Re-105A/pBifiCD)

A vial charged with 10 mL ($2.3\times10^9$ cfu/mL) was thawed in a hot water bath at 37 degree C. for 10 minutes immediately before use.

Preparation Method and Preparation Frequency for 5-FC

A required amount of 5-FC was precisely measured. Water for injection was added thereto, and the mixture was treated using an ultrasonic device for 20 minutes, thus giving a 12.5 mg/mL solution. The storage and use of the administration liquids were limited to the day of preparation, and 1st to 3rd administration liquids were prepared at the same time. The administration liquids were stored at room temperature under shade until all administrations were completed.

Preparation method and preparation frequency for maltose and physiological saline Maltose or physiological saline was used by dispensing on the day of administration. Storage and use of the administration liquids were limited to the day of preparation, and 1st and 2nd administration liquids were prepared at the same time. The administration liquids were stored at room temperature under shade until all administrations were completed.

(5) Administration Frequency, Administration Time, and Administration Period

Bacteria (*B. longum* Re-105A/pBifiCD)

On Day 1 to Day 3, administration to the second to fourth groups was carried out once a day (7.30 to 12.00) for 3 days.

5-FC

On Day 5 to Day 25, administration to the second to fourth groups was carried out three times a day (at intervals of about 4 hours), and on Day 26 administration was carried out once, for a total of 64 administrations.

Maltose and Physiological Saline

On Day 1 to Day 25, administration to the second to fourth groups was carried out twice a day, for a total of 50 administrations. The administration interval was at least 6 hours. On Day 1 to Day 3, since the first administration was carried out after at least one hour had elapsed after administration of bacteria (*B. longum* Re-105A/pBifiCD) was completed, the administration interval was 3 to 4 hours.

(6) Administration Method

Bacteria (*B. longum* Re-105A/pBifiCD)

A nude rat was retained, and an administration liquid was continuously administered into the tail vein using a 10 mL syringe (Terumo Corp.), a 25 G winged intravenous injection needle (Terumo Corp.), and a syringe pump (TE-3315, Terumo Corp.).

5-FC

Orally administered using a 5 mL syringe (Terumo Corp.) and a stomach tube (RZ-1, made from Teflon, CLEA Japan Inc.).

Maltose and Physiological Saline

Intraperitoneally administered using a 2.5 mL syringe (Terumo Corp.) and a 27 G injection needle (NIPRO).

(7) Dose

Bacteria (*B. longum* Re-105A/pBifiCD)

$1\times10^{10}$ cfu/kg/day (second group: 1.4 to $1.8\times10^9$ cfu/body/day) or $4\times10^{10}$ cfu/kg/day (third group: 5.8 to $7.0\times10^9$ cfu/body/day, fourth group: 6.0 to $6.7\times10^9$ cfu/body/day). The administration rate was 10 mL/kg/hr. The administration rate was calculated from the weight of the rat on Day 1, and rounded off to the first decimal place.

5-FC 750 mg/kg/day (250 mg/kg/time). The administration volume was 60 mL/kg/day (20 mL/kg/time). The amount of administration liquid was calculated from the latest weight of the rat, and rounded off to the first decimal place.

Maltose and Physiological Saline

The dose of maltose was 200 mg/body/day (100 mg/body/time), and the dose of physiological saline was 0 mg/body/day (expressed as amount of maltose). The administration volume was 2 mL/body/day (1 mL/body/time).

(8) Measurement of Tumor Diameter

Calculation of Tumor Volume

After transplantation of tumor cells, the major diameter and the minor diameter of the tumor were measured using calipers, and the tumor volume was determined from the equation below. From the day of grouping onward, measurement of tumor diameter was carried out on Day 0, 5, 8, 11, 14, 17, 20, 23, and 26.

Tumor volume ($mm^3$)=major diameter (mm)×minor diameter (mm)×minor diameter (mm)/2

Calculation of Tumor Growth Rate

Tumor growth rate was calculated in accordance with the equation below from the tumor volume at the start of administration of 5-FC onward.

Tumor growth rate=tumor volume from Day 5 onward/tumor volume on Day 5

Calculation of T/C(%)

T/C(%) was calculated in accordance with the equation below from the tumor growth rate from Day 8 onward.

T/C(%)=average tumor growth rate of the second, third, or fourth group/average tumor growth rate of first group×100

(9) Results

Tumor Volume

Figure 2:
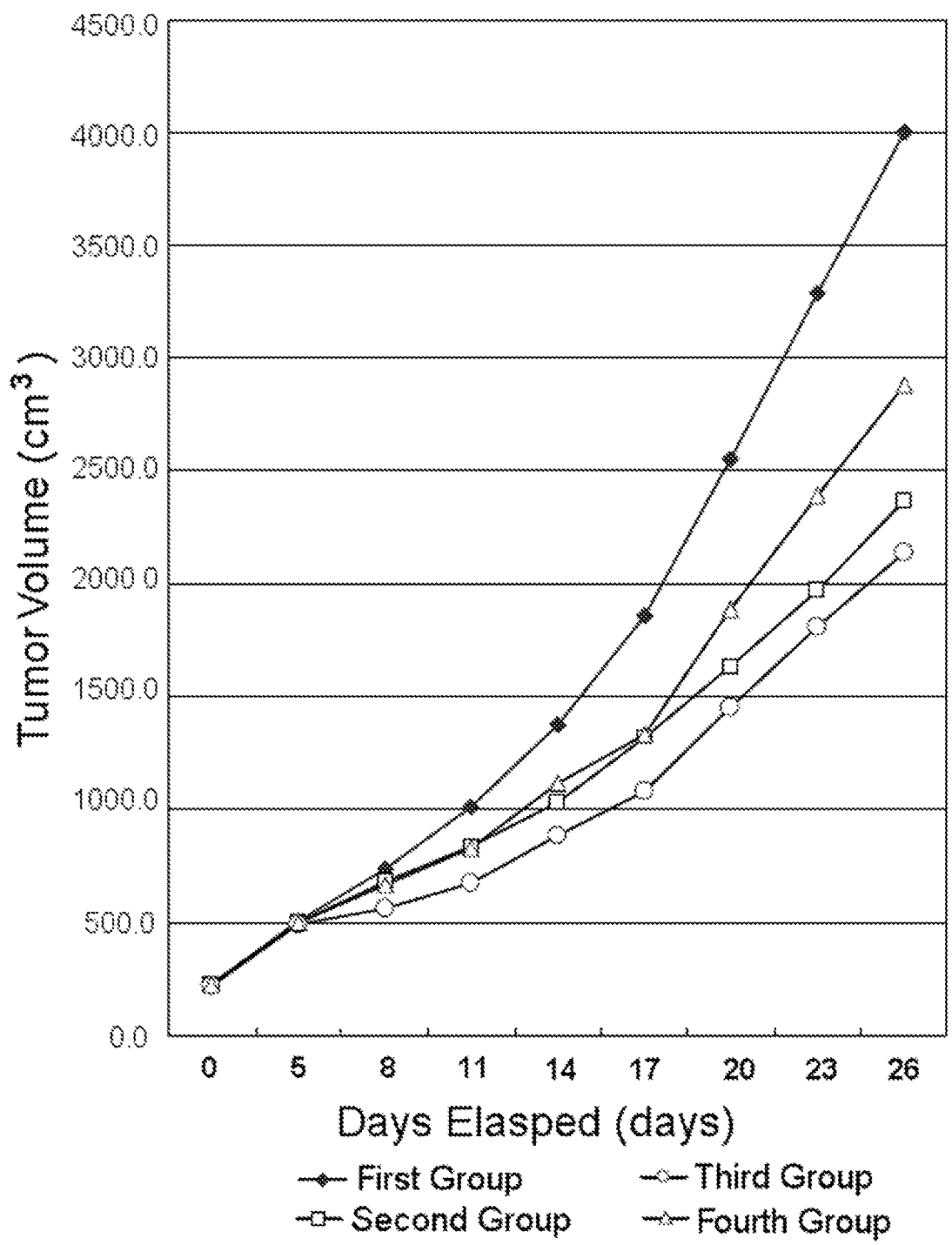
FIG. 2 is a diagram showing the tumor proliferation suppression effect from the combined use of *B. longum* Re-105A/pBifiCD and maltose.

The results of measurement of tumor volume are given in Table 8 and FIG. 2.

The tumor volume of the first group (untreated group) was 223.3 plus/minus 43.0 $mm^3$ on Day 0 and 505.0 plus/minus 125.9 $mm^3$ on Day 5. On Day 26, it was 4002.6 plus/minus 661.1 $mm^3$. The tumor volume increased markedly over the examination period.

The tumor volume of the second group (low bacterial dose, maltose-administered) was 221.0 plus/minus 44.4 $mm^3$ on Day 0, and 496.1 plus/minus 108.3 $mm^3$ on Day 5, on which administration of 5-FC was started. Furthermore, on Day 26 it was 2370.9 plus/minus 487.4 $mm^3$. For the second group, compared with the first group, a significantly lower value for the tumor volume was observed at all times from Day 11 onward (on Day 11 P<0.05, on Day 14, 17, 20, 23, and 26 P<0.001: Student's t-test).

The tumor volume of the third group (high bacterial dose, maltose-administered) was 219.7 plus/minus 41.9 $mm^3$ on Day 0, and 488.7 plus/minus 80.2 $mm^3$ on Day 5, on which administration of 5-FC was started. Furthermore, on Day 26 it was 2135.6 plus/minus 592.9 $mm^3$. For the third group, compared with the first group, a significantly lower value for the tumor volume was observed at all times from Day 8 onward (on Day 8 P<0.01, Day 11, 14, 17, 20, 23, and 26 P<0.001: Student's t-test) and, furthermore, compared with the fourth group, a significantly lower value for the tumor volume was observed on Day 14, 20, 23, and 26 (on all P<0.05: Student's t-test).

The tumor volume of the fourth group (high bacterial dose, non-maltose-administered) was 222.1 plus/minus 43.5 $mm^3$ on Day 0, and 500.3 plus/minus 109.3 $mm^3$ on Day 5, on which administration of 5-FC was started. Furthermore, on Day 26 it was 2879.3 plus/minus 658.4 $mm^3$. For the fourth group, compared with the first group, a significantly lower value for the tumor volume was observed at all times from Day 11 onward (on Day 14 P<0.05, on Day 11, 17, 20, 23, and 26 P<0.01: Student's t-test).

TABLE 8

Tumor volume (average value)

| Group | Number of animals | Day 0 | Day 5 | Day 8 | Day 11 | Day 14 | Day 17 | Day 20 | Day 23 | Day 26 |
|---|---|---|---|---|---|---|---|---|---|---|
| | | Tumor volume ($mm^3$) (average value) | | | | | | | | |
| First group | 8 | 223.3 ± 43.0 | 505.0 ± 125.9 | 736.1 ± 112.6 | 1006.3 ± 106.4 | 1370.7 ± 155.5 | 1860.2 ± 303.6 | 2547.9 ± 426.4 | 3288.3 ± 566.4 | 4002.6 ± 661.1 |
| Second group | 8 | 221.0 ± 44.4 | 496.1 ± 108.3 | 683.4 ± 134.6 | 835.5 ± 143.8 | 1032.7 ± 149.0 | 1320.7 ± 160.4 | 1633.7 ± 249.8 | 1970.2 ± 341.0 | 2370.9 ± 487.4 |
| Third group | 8 | 219.7 ± 41.9 | 488.7 ± 80.2 | 562.8 ± 113.3 | 673.8 ± 177.4 | 885.1 ± 206.0 | 1078.0 ± 265.3 | 1450.2 ± 356.1 | 1807.3 ± 488.3 | 2135.6 ± 592.9 |
| Fourth group | 8 | 222.1 ± 43.5 | 500.3 ± 109.3 | 662.7 ± 129.9 | 827.8 ± 116.4 | 1117.9 ± 183.3 | 1334.3 ± 216.7 | 1884.1 ± 353.6 | 2388.2 ± 477.9 | 2879.3 ± 658.4 |

Tumor Growth Rate

The results are given in Table 9.

The tumor growth rate of the first group was 8.4 plus/minus 2.7 on Day 26.

Compared with the first group, the tumor growth rate of the second group was a significantly lower value at all times from Day 17 onward (on Day 17, 20, and 23 P<0.05, on Day 26 P<0.01: Student's t-test), and on Day 26 it was 4.9 plus/minus 1.2. Compared with the first group and the fourth group, the tumor growth rate of the third group was a significantly lower value at all times from Day 8 onward (compared with the first group P<0.01 and compared with the fourth group P<0.05 at all times: Student's t-test), and on Day 26 it was 4.4 plus/minus 0.8.

Compared with the first group, the tumor growth rate of the fourth group was a significantly lower value at all times from Day 17 onward (all thereof P<0.05: Student's t-test), and on Day 26 it was 5.9 plus/minus 1.4.

TABLE 9

| | | Tumor growth rate (average value) | | | | | | | |
|---|---|---|---|---|---|---|---|---|---|
| Group | Number of animals | Day 5 | Day 8 | Day 11 | Day 14 | Day 17 | Day 20 | Day 23 | Day 26 |
| First group | 8 | 1.0 ± 0.0 | 1.5 ± 0.3 | 2.1 ± 0.5 | 2.9 ± 0.9 | 3.9 ± 1.1 | 5.3 ± 1.6 | 6.9 ± 2.3 | 8.4 ± 2.7 |
| Second group | 8 | 1.0 ± 0.0 | 1.4 ± 0.2 | 1.7 ± 0.3 | 2.2 ± 0.6 | 2.8 ± 0.9 | 3.5 ± 1.2 | 4.2 ± 1.2 | 4.9 ± 1.2 |
| Third group | 8 | 1.0 ± 0.0 | 1.2 ± 0.1 | 1.4 ± 0.3 | 1.8 ± 0.2 | 2.2 ± 0.3 | 3.0 ± 0.4 | 3.7 ± 0.7 | 4.4 ± 0.8 |
| Fourth group | 8 | 1.0 ± 0.0 | 1.3 ± 0.1 | 1.7 ± 0.2 | 2.3 ± 0.4 | 2.7 ± 0.6 | 3.9 ± 0.8 | 4.9 ± 1.0 | 5.9 ± 1.4 |

T/C(%)
The results are given in Table 10.
T/C(%) of the second group on Day 26 was 58.3.
T/C(%) of the third group on Day 26 was 52.4.
T/C(%) of the fourth group on Day 26 was 70.2.

TABLE 10

| | | T/C (%) | | | | | | |
|---|---|---|---|---|---|---|---|---|
| Group | Number of animals | Day 8 | Day 11 | Day 14 | Day 17 | Day 20 | Day 23 | Day 26 |
| First group | 8 | — | — | — | — | — | — | — |
| Second group | 8 | 93.3 | 81.0 | 75.9 | 71.8 | 66.0 | 60.9 | 58.3 |
| Third group | 8 | 80.0 | 66.7 | 62.1 | 56.4 | 56.6 | 53.9 | 52.4 |
| Fourth group | 8 | 86.7 | 81.0 | 79.3 | 69.2 | 73.6 | 71.0 | 70.2 |

From the results of this test, it was confirmed that maltose exhibits an effect in promoting specific colonization of *B. longum* Re-105A/pBifiCD in tumor tissue, and an effect in promoting proliferation and an effect in maintaining proliferation in tumor tissue.

Furthermore, in accordance with the use of maltose in combination, it is possible for a low dose of bacteria to exhibit an antitumor effect at the same level as that of a high dose of bacteria, it is therefore possible to reduce the dose of bacteria, and it has been confirmed that a safe treatment that has a low burden on a patient and causes fewer side effects can be carried out.

Use of *B. longum* Re-105A/pBifiCD and Maltose or Lactulose in Combination (1) Preparation of Tumor-Bearing Nude Mouse and Measurement of Tumor Volume Preparation of tumor-bearing nude mice and measurement of tumor volume were carried out in the same manner as in Example 1 and Example 2.

(2) Grouping and Administration of Test Drug

32 KPL-1 tumor-bearing mice having a tumor volume of 60 to 90 mm³ were selected and divided into four groups (8 mice per group), and each test drug was administered in accordance with the group constitution and administration schedule shown in (3) below.

Administration of Bacteria (*B. longum* Re-105A/pBifiCD)
With regard to bacteria (*B. longum* Re-105A/pBifiCD), in accordance with (3) Group constitution and administration schedule, *B. longum* Re-105A/pBifiCD frozen preparation ($2.3 \times 10^9$ cfu/mL) was intravenously administered at 0.3 mL per mouse twice a day for 3 days (Day 1 to 3). The total dose of the bacteria was $4.1 \times 10^9$ cfu/mouse.

Administration of Flucytosine (5-FC)
0.4 mL of a 12.5 mg/mL 5-FC solution was orally administered (750 mg/kg/day) twice a day to mice of two groups excluding the control group (group A) in accordance with the group constitution and administration schedule shown in (3). The administration period was 21 days (Day 4 to 24) from the day after final administration of the bacteria.

Administration of Maltose
In accordance with the group constitution and administration schedule shown in (3), 1 mL of a 10% maltose injection was intraperitoneally administered to mice twice a day. The administration period was 24 days (Day 1 to 24) from the day of administration of bacteria (*B. longum* Re-105A/pBifiCD).

For group D, instead of maltose, the same amount of physiological saline was administered on the same schedule (Day 1 to 24).

Administration of Lactulose
1 mL of a 20% (w/v) lactulose solution dissolved in purified water was intraperitoneally administered once a day to mice in accordance with the group constitution and administration schedule shown in (3). The administration period was 24 days (Day 1 to 24) from the day of administration of the bacteria, but since it was confirmed that two mice had died during the administration period (Day 13 and Day 19) the administration schedule was changed, and administration from Day 19 onward was suspended.

(3) Summary of Group Constitution and Administration Schedule

The group constitution and the administration schedule are shown in Table 11.

TABLE 11

| | Group constitution and administration schedule | | | |
|---|---|---|---|---|
| Group | Substance administered | Dose per day | Administration day (Day) | Number of animals |
| Group A | Bacteria | — | — | 8 |
| | 5-FC | — | — | |
| | Saccharide | — | — | |

TABLE 11-continued

Group constitution and administration schedule

| Group | Substance administered | Dose per day | Administration day (Day) | Number of animals |
|---|---|---|---|---|
| Group B | Bacteria (2.3 × 10⁹ cfu/mL) | 0.6 mL (1.38 × 10⁹ cfu/day) | 1 to 3 | 8 |
|  | 5-FC (12.5 mg/mL) | 1.2 mL (750 mg/kg/day) | 4 to 24 |  |
|  | Maltose (10%) | 2 mL (200 mg/day) | 1 to 24 |  |
| Group C | Bacteria (2.3 × 10⁹ cfu/mL) | 0.6 mL (1.38 × 10⁹ cfu/day) | 1 to 3 | 8 |
|  | 5-FC (12.5 mg/mL) | 1.2 mL (750 mg/kg/day) | 4 to 24 |  |
|  | Lactulose (20%) | 1 mL (200 mg/day) | 1 to 24 |  |
| Group D | Bacteria (2.3 × 10⁹ cfu/mL) | 0.6 mL (1.38 × 10⁹ cfu/day) | 1 to 3 | 8 |
|  | 5-FC (12.5 mg/mL) | 1.2 mL (750 mg/kg/day) | 4 to 24 |  |
|  | Saccharide | — | 1 to 24 |  |

Note)
*Physiological saline administered to group D instead of saccharide (maltose or lactulose).

(4) Measurement of Number of Bacteria within Tumor

5-FC was orally administered on the test observation final day (Day 25) and the following day (Day 26), after 1 hour the mouse was sacrificed, the tumor was removed, the weight (g) was measured, and it was then homogenized using an anaerobic diluent.

The number of bacteria within the tumor was calculated in the same manner as in Example 1, (3).

(5) Results

The tumor volume of mice of each group was measured chronologically and expressed as an average value plus/minus SD. Tumor volume ratio [T/C(%)] relative to the control group was used as a criterion in the antitumor effect assessment.

Tumor volume changes in the control group (group A) and the groups to which bacteria (*B. longum* Re-105A/pBifiCD) and saccharide were administered in combination and the tumor growth rate of tumor volume on Day 25 relative to the tumor volume on Day 4 are shown in Table 12.

Furthermore, T/C (%) as the criterion for the antitumor effect is shown in Table 13. Whereas the T/C of the non-saccharide-using group (group D) on Day 25 was 51.3(%) (Student's t-test: p=0.013), the T/C of the maltose combined-use group (group B) was 38.5(%) (p=0.003), and the T/C of the lactulose combined-use group (group C) was 35.0(%) (p=0.002), thus exhibiting an effect in enhancing suppression of tumor growth in both cases.

TABLE 13

| Group | Number of animals | T/C (%) Day 7 | T/C (%) Day 11 | T/C (%) Day 14 | T/C (%) Day 18 | T/C (%) Day 21 | T/C (%) Day 25 | Student's t-test |
|---|---|---|---|---|---|---|---|---|
| Group A | 8 | — | — | — | — | — | — |  |
| Group B | 8 | 68.9 | 62.7 | 53.2 | 47.7 | 44.7 | 38.5 | P = 0.003 |
| Group C | 6* | 72.1 | 78.4 | 64.3 | 44.3 | 36.9 | 35.0 | P = 0.002 |
| Group D | 8 | 52.1 | 68.5 | 57.7 | 50.9 | 50.7 | 51.3 | P = 0.013 |

Note)
*2 out of 8 mice died during test.

From the results of this test, it can be confirmed that in the same manner as that of maltose, lactulose also exhibits an effect in promoting specific colonization of *B. longum* Re-105A/pBifiCD in tumor tissue, and an effect in promoting proliferation and an effect in maintaining proliferation, and can enhance the antitumor effect of *B. longum* Re-105A/pBifiCD.

TABLE 12

Tumor volume (average value) and tumor growth rate

| Group | Number of animals | Tumor volume (mm³) (average value) Day 0 | Day 4 | Day 7 | Day 11 | Day 14 | Day 18 | Day 21 | Day 25 | Tumor growth rate (%) |
|---|---|---|---|---|---|---|---|---|---|---|
| Group A | 8 | 74.8 ± 8.5 | 150.9 ± 25.2 | 229.6 ± 45.1 | 358.1 ± 107.7 | 575.4 ± 161.0 | 864.1 ± 247.5 | 1222.3 ± 413.6 | 1906.1 ± 762.0 | 12.8 |
| Group B | 8 | 75.0 ± 8.7 | 119.0 ± 35.1 | 158.3 ± 61.7 | 224.4 ± 106.4 | 306.0 ± 129.0 | 412.4 ± 202.7 | 546.4 ± 322.5 | 734.6 ± 494.0 | 5.9 |
| Group C | 6* | 75.4 ± 10.7 | 120.2 ± 43.8 | 165.6 ± 96.5 | 280.9 ± 213.4 | 370.0 ± 260.6 | 382.6 ± 267.2 | 451.1 ± 296.3 | 667.4 ± 292.9 | 5.6 |
| Group D | 8 | 73.7 ± 8.7 | 95.3 ± 21.2 | 119.7 ± 23.7 | 245.2 ± 70.6 | 331.8 ± 121.7 | 439.5 ± 213.9 | 620.2 ± 254.6 | 978.5 ± 505.1 | 10.1 |

Note)
*2 out of 8 mice died during test.

INDUSTRIAL APPLICABILITY

The expression vector of the present invention can provide an extremely safe gene transporter for introducing an anaerobic microorganism an exogenous gene with therapeutic or prophylactic use without a risk of horizontal transfer to other pathogenic or aerobic/facultatively anaerobic microorganisms such as E. coli, and even if a horizontal transfer occurs, the vector will not replicated in microorganisms other than the transformant, since the vector does not comprise an origin of replication of such other microorganism.

Further, the colonization and proliferation enhancer for the transformed microorganism of the present invention improves the therapeutic effect of the transformed microorganism of the present invention, enabling the reduction of the dosage of the transformed microorganism while rendering an equal therapeutic effect, thereby reducing the burden of the patient to be treated.

Further, the therapeutic agent of the present invention comprising in combination a pharmaceutical composition comprising the transformed anaerobic microorganism and a pharmaceutical composition comprising the colonization and proliferation enhancer has a utility as a therapeutic agent for an anaerobic disease, with an improved therapeutic effect and reduced effective required dose, as well as an improved safety in both environmental and therapeutic point of view.

The invention claimed is:

1. A therapeutic agent comprising:
(i) a pharmaceutical composition comprising an obligately anaerobic microorganism that has been transformed by an expression vector that functions in the obligately anaerobic microorganism, wherein the expression vector does not contain a plasmid replication unit that functions in wild-type *E. coli* and wherein the expression vector comprises: (1) a plasmid replication unit that functions in an obligately anaerobic microorganism but does not function in wild-type *E. coli*, and (2) a protein expression unit comprising DNA that encodes (a) a promoter that functions in the obligately anaerobic microorganism, (b) a protein with antitumor activity or a protein capable of converting an antitumor substance precursor into an antitumor substance, and (c) a terminator that functions in the obligately anaerobic microorganism; and
(ii) a pharmaceutical composition comprising a colonization and proliferation enhancer for the obligately anaerobic microorganism.

2. The therapeutic agent according to claim 1, wherein the protein with therapeutic activity is a protein capable of converting an antitumor substance precursor into an antitumor substance.

3. The therapeutic agent according to claim 1, wherein the obligately anaerobic microorganism is selected from the group consisting of *Bifidobacterium*, *Lactobacillus*, *Enterococcus*, *Streptococcus*, and *Clostridium*.

4. The therapeutic agent according to claim 3, wherein the obligately anaerobic microorganism is *Bifidobacterium*.

5. The therapeutic agent according to claim 4, wherein the *Bifidobacterium* is selected from the group consisting of *Bifidobacterium* (*B.*) *adolescentis*, *B. animalis*, *B. infantis*, *B. thermophilum*, *B. pseudolongum*, *B. bifidum*, *B. breve*, and *B. longum*.

6. The therapeutic agent according to claim 5, wherein the *Bifidobacterium* is *B. longum*.

7. The therapeutic agent according to claim 6, wherein the *Bifidobacterium* is *B. longum* 105-A/pBifiCD (Patent Microorganisms Depositary (NPMD) Accession Number NITE BP-491).

8. The therapeutic agent according to claim 2, wherein the protein is selected from the group consisting of cytosine deaminase, nitroreductase, and b-glucuronidase.

9. The therapeutic agent according to claim 8, wherein the protein is cytosine deaminase.

10. The therapeutic agent according to claim 1, wherein the colonization and proliferation enhancer is selected from the group consisting of arabinose, xylose, galactose, glucose, maltose, lactose, melibiose, melezitose, raffinose, and lactulose.

11. The therapeutic agent according to claim 10, wherein the colonization and proliferation enhancer is glucose or maltose.

12. The therapeutic agent according to claim 11, wherein the colonization and proliferation enhancer is maltose.

13. The therapeutic agent according to claim 1, wherein the pharmaceutical composition comprising a colonization and proliferation enhancer is formulated for intravenous administration.

14. The therapeutic agent according to claim 13, wherein the colonization and proliferation enhancer comprises glucose or maltose.

15. The therapeutic agent according to claim 2, further comprising a pharmaceutical composition comprising an antitumor substance precursor that is converted into an antitumor substance by said protein that is capable of converting an antitumor substance precursor into an antitumor substance.

16. The therapeutic agent according to claim 15, wherein the antitumor substance precursor is 5-fluorocytosine and wherein the protein is cytosine deaminase.

17. The therapeutic agent according to claim 1, wherein the pharmaceutical composition comprising an obligately anaerobic microorganism is formulated for intravenous administration.

18. The therapeutic agent according to claim 1, wherein the pharmaceutical composition of (i) and the pharmaceutical composition of (ii) are mixed to form a single pharmaceutical composition.

19. The therapeutic agent according to claim 1, wherein the pharmaceutical composition of (i) and the pharmaceutical composition of (ii) are formulated separately.

20. A method for treating a solid tumor in a patient in need of such treatment, comprising administering to said patient the therapeutic agent according to claim 1.

* * * * *

UNITED STATES PATENT AND TRADEMARK OFFICE
CERTIFICATE OF CORRECTION

PATENT NO. : 8,470,311 B2
APPLICATION NO. : 12/988181
DATED : June 25, 2013
INVENTOR(S) : Sasaki et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 301 days.

Signed and Sealed this
Eighth Day of September, 2015

Michelle K. Lee
*Director of the United States Patent and Trademark Office*

```
                       SEQUENCE LISTING

<160> NUMBER OF SEQ ID NOS: 1

<210> SEQ ID NO 1
<211> LENGTH: 4476
<212> TYPE: DNA
<213> ORGANISM: Artificial
<220> FEATURE:
<223> OTHER INFORMATION: plasmid pBifiCD

<400> SEQUENCE: 1
agatccgtct tcctgctggc ctatgcattg ggttccgcag tgcccactcc aggcggtctg      60
ggcggtgtgg aagcggcgct gacattcgcg ttcgtggcgg tcggagtgcc gcagggcgtg     120
gcgctttccg ccactttgct gcaccgcgtg gtgttctact ggctgcgcat tccgctgggc     180
gcggcggcca tgaagtggct tgacaagcat aatcttgtct gattcgtcta ttttcatacc     240
cccttcgggg aaatagatgt gaaaacccctt ataaaacgcg ggttttcgca gaaacatgcg     300
ctagtatcat tgatgacaac atggactaag caaaagtgct tgtcccctga cccaagaagg     360
atgctttatg gcatacaaca agtctgacct cgtttcgaat aacgctttac aaacaattat     420
taacgcccgg ttaccaggcg aagagggct gtggcagatt catctgcagg acggaaaaat      480
cagcgccatt gatgcgcaat ccggcgtgat gcccataact gaaaacagcc tggatgccga     540
acaaggttta gttataccgc cgtttgtgga gccacatatt cacctggaca ccacgcaaac     600
cgccggacaa ccgaactgga atcagtccgg cacgctgttt gaaggcattg aacgctgggc     660
cgagcgcaaa gcgttattaa cccatgacga tgtgaaacaa cgcgcatggc aaacgctgaa     720
atggcagatt gccaacggca ttcagcatgt gcgtacccat gtcgatgttt cggatgcaac     780
gctaactgcg ctgaaagcaa tgctggaagt gaagcaggaa gtcgcgccgt ggattgatct     840
gcaaatcgtc gccttccctc aggaagggat tttgtcgtat cccaacggtg aagcgttgct     900
ggaagaggcg ttacgcttag gggcagatgt agtgggggcg attccgcatt ttgaatttac     960
ccgtgaatac ggcgtggagt cgctgcataa aaccttcgcc ctggcgcaaa aatacgaccg    1020
tctcatcgac gttcactgtg atgagatcga tgacgagcag tcgcgctttg tcgaaaccgt    1080
tgctgccctg gcgcaccatg aaggcatggg cgcgcgagtc accgccagcc acaccacggc    1140
aatgcactcc tataacgggg cgtataccct acgcctgttc cgcttgctga aaatgtccgg    1200
tattaacttt gtcgccaacc cgctggtcaa tattcatctg caaggacgtt tcgatacgta    1260
tccaaaacgt cgcggcatca cgcgcgttaa agagatgctg gagtccggca ttaacgtctg    1320
ctttggtcac gatgctgtct tcgatccgtg gtatccgctg ggaacggcga atatgctgca    1380
agtgctgcat atgggctgc atgtttgcca gttgatgggc tacgggcaga ttaacgatgg    1440
cctgaattta atcacccacc acagcgcaag gacgttgaat ttgcaggatt acggcattgc    1500
```

```
cgccggaaac agcgccaacc tgattatcct gccggctgaa aatgggtttg atgcgctgcg    1560
ccgtcaggtt ccggtacgtt attcggtacg tggcggcaag gtgattgcca gcacacaacc    1620
ggcacaaacc accgtatatc tggagcagcc agaagccatc gattacaaac gttgaccttc    1680
tgctcgtagc gattacttcg agcattactg acgacaaaga ccccgaccga gatggtcggg    1740
gtcttttgt tgtggtgctg tgacgtgttg tccaaccgta ttattccgga ctagtcctcc    1800
aggacctcgt ctacgaggcg ctgagcgagg aatggcgcaa aagggacggc gagatcagcg    1860
acccatgggc caacgacgag gcggacggat accagccgcc ctcatacgag ccggtcaacc    1920
ccgaacgcag gactccccag acgccctccg atggcctgat ctgacgtccg aaaaaaggcg    1980
ctgtgcgccc ttttaaatc ttttataaat cttttacat tcttttagcc cctccgcagc    2040
cttactctcc aacgggttt cagccgaaac ctacaccaaa aggggagcga acctacacca    2100
aaagggagc gaacctacac caaaagggga gcgaacctac accaaaaggg gagctatata    2160
caccttttgt tatttaaggt gcaagttgtg ctatgctgag gccatgtcca atgagatcgt    2220
gaagttcagc aaccagttca caacgtcgc gctgaagaag ttcgacgccg tgcacctgga    2280
cgtgctcatg gcgatcgcct caagggtgag ggagaagggc acggccacgg tggagttctc    2340
gttcgaggag ctgcgcggcc tcatgcgatt gaggaagaac ctgaccaaca agcagctggc    2400
cgacaagatc gtgcagacga acgcgcgcct gctggcgctg aactacatgt tcgaggattc    2460
gggcaagatc atccagttcg cgctgttcac gaagttcgtc accgacccgc aggaggcgac    2520
tctcgcggtt ggggtcaacg aggagttcgc gttcctgctc aacgacctga ccagccagtt    2580
cacgcgcttc gagctggccg agttcgccga cctcaagagc aagtacgcca aggagttcta    2640
ccgcagggcc aagcagtacc gcagctccgg aatctggaag atcggccgcg acgagttctg    2700
ccgactgctt ggcgttccac cgtcggcaat aacccagaca cgatatctga atcagaaggt    2760
tcttcagcca attcaggagg agtgtgggcc tctccttggc ctgaagatcg agcgccagta    2820
cgtgaaacgc aggctgtcgg gcttcgtgtt cacattcgcc cgcgagaccc ctccggtgat    2880
cgacgccagg cccgtggagg cgaggaagac ggacggcgac ggcaagggcc attgacgag    2940
cgttgccggg tacggcgagg tgttcacgac cacggcgttg ttcgacgtga cggccgcccg    3000
ggctcacttc gacggcaccg ttgaagccgg ggagtgccgt ttctgcgcgt ttgacgcgcg    3060
caaccgcgaa catcatgcgc ggaacgccgg aaggctgttc tagcggccgt gtccgcgcct    3120
ctggggcggt tgcgcctgcc atgggtcgat ctgccgctgt tcggcctcac gctggtctgt    3180
gcgctgcctg atctccctga gcaggtcggc cttggtcctg ggggcgcttc gctcctcgaa    3240
cgggccgctc tcccccaggt cctcgggctc gctcaggtcc aacggctcgt caccggacgg    3300
ctcgggccgg ttctctccct gtgccgggtt ctccgcctgt gcgcgttgtt cggccatgcg    3360
cagtgcgagg gccttcacct gttcgggct tgtcgactcg attttcgttc gtgaatacat    3420
gttataataa ctataactaa taacgtaacg tgactggcaa gagatatttt taaaacaatg    3480
aataggttta cacttacttt agttttatgg aaatgaaaga tcatatcata tataatctag    3540
aataaaatta actaaaataa ttattatcta gataaaaat ttagaagcca atgaaatcta    3600
taaataaact aaattaagtt tatttaatta acaactatgg atataaaata ggtactaatc    3660
aaaatagtga ggaggatata tttgaataca tacgaacaaa ttaataaagt gaaaaaaata    3720
cttcggaaac atttaaaaaa taaccttatt ggtacttaca tgtttggatc aggagttgag    3780
agtggactaa aaccaaatag tgatcttgac ttttagtcg tcgtatctga accattgaca    3840
gatcaaagta aagaaatact tatacaaaaa attagaccta tttcaaaaaa aataggagat    3900
```

```
aaaagcaact tacgatatat tgaattaaca attattattc agcaagaaat ggtaccgtgg   3960
aatcatcctc ccaaacaaga atttatttat ggagaatggt tacaagagct ttatgaacaa   4020
ggatacattc ctcagaagga attaaattca gatttaacca taatgcttta ccaagcaaaa   4080
cgaaaaaata aaagaatata cggaaattat gacttagagg aattactacc tgatattcca   4140
ttttctgatg tgagaagagc cattatggat tcgtcagagg aattaataga taattatcag   4200
gatgatgaaa ccaactctat attaacttta tgccgtatga ttttaactat ggacacgggt   4260
aaaatcatac caaaagatat tgcgggaaat gcagtggctg aatcttctcc attagaacat   4320
agggagagaa ttttgttagc agttcgtagt tatcttggag agaatattga atggactaat   4380
gaaaatgtaa atttaactat aaactattta aataacagat taaaaaaatt ataaaaaaat   4440
tgaaaaaatg gtggaaacac tttttttcaat tttttt                            4476
```